United States Patent
Kawabata et al.

(10) Patent No.: US 6,468,995 B1
(45) Date of Patent: *Oct. 22, 2002

(54) CEPHEM COMPOUNDS

(75) Inventors: Kohji Kawabata, Kawanishi (JP); Takeshi Terasawa, Kawachinagano (JP); Ayako Ohki, Takarazuka (JP); Fumiyuki Shirai, Osaka (JP); Hirofumi Yamamoto, Ikeda (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/781,924

(22) Filed: Dec. 30, 1996

Related U.S. Application Data

(63) Continuation of application No. 08/400,770, filed on Mar. 8, 1995, now abandoned, which is a continuation-in-part of application No. 08/392,740, filed as application No. PCT/JP94/01488 on Sep. 8, 1994, now abandoned.

(30) Foreign Application Priority Data

| Sep. 9, 1993 | (GB) | 9318678 |
| Dec. 8, 1993 | (GB) | 9325104 |
| Dec. 31, 1993 | (GB) | 9326612 |

(51) Int. Cl.⁷ ............... C07D 501/34; A61K 31/546
(52) U.S. Cl. ................. 514/210.05; 540/227
(58) Field of Search .................. 540/227; 514/210.05

(56) References Cited

U.S. PATENT DOCUMENTS

| 5,110,921 A |   | 5/1992 | Takaya et al. ............ 540/222 |
| 5,332,731 A | * | 7/1994 | Yamamoto et al. ........ 540/227 |
| 5,498,777 A | * | 3/1996 | Cama et al. ............... 540/227 |
| 5,583,216 A | * | 12/1996 | Ochiai et al. ............. 540/222 |

* cited by examiner

Primary Examiner—John M. Ford
(74) Attorney, Agent, or Firm—Oblon, Spivak, McClelland, Maier & Neustadt, P.C.

(57) ABSTRACT

A compound of the formula:

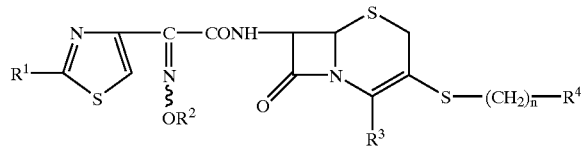

wherein $R^1$ is amino or protected amino;

$R^2$ is hydrogen, lower alkyl or hydroxy protective group;

$R^3$ is carboxy or protected carboxy;

$R^4$ is an unsubstituted 5, 6 or 7-membered heteromonocyclic group containing two nitrogen atoms as heteroatoms, and which optionally further contains one oxygen or sulfur atom; or $R^4$ is said 5, 6 or 7-membered heteromonocyclic group substituted by 1 to 4 groups selected from the group consisting of lower alkyl, lower alkoxy, lower alkylthio, lower alkylamino, cyclo(lower)alkyl, cyclo(lower)alkenyl, halogen, amino, protected amino, protected hydroxy, cyano, nitro, carboxy, hydroxy(lower)alkyl, amino(lower)alkyl, and carbamoyloxy; and n is 1 or 2.

20 Claims, No Drawings

CEPHEM COMPOUNDS

This application is a Continuation of application Ser. No. 08/400,770, filed on Mar. 8, 1995, now abandoned, which is a Continuation-In-Part of Ser. No. 08/392,740 filed Mar. 7, 1995, now abandoned, which was filed as International Application No. PCT/JP94/01488, filed Sep. 8, 1994.

TECHNICAL FIELD

This invention relates to new cephem compounds and pharmaceutically acceptable salts thereof which are useful as a medicament.

BACKGROUND ART

Some cephem compounds have been known as described, for example, in Japanese Kokai H2-134385.

DISCLOSURE OF INVENTION

The present invention relates to new cephem compounds and pharmaceutically acceptable salts thereof.

More particularly, it relates to new cephem compounds and pharmaceutically acceptable salts thereof, which have antimicrobial activities, to processes for preparation thereof, to pharmaceutical composition comprising the same and to a method for treating infectious diseases in human being and animals.

Accordingly, one object of the present invention is to provide the cephem compounds and pharmaceutically acceptable salts thereof, which show highly active against a number of pathogenic microorganisms.

Another object of the present invention is to provide processes for the preparation of the cephem compounds and salts thereof.

A further object of the present invention is to provide pharmaceutical compositions comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula (I):

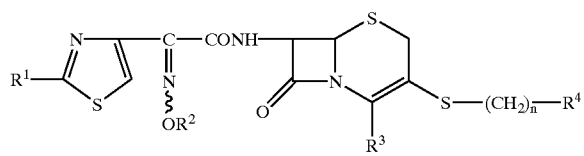

(I)

wherein $R^1$ is amino or protected amino,
$R^2$ is hydrogen, lower alkyl or hydroxy protective group,
$R^3$ is carboxy or protected carboxy,
$R^4$ is 3-pyridyl, 4-pyridyl or optionally substituted heteromonocyclic group containing two nitrogen atoms as hetero atoms, and which may also contain one oxygen or sulfur atom, and
n is 0, 1 or 2, provided that when $R^2$ is lower alkyl, then n is 1 or 2, and
$R^4$ is optionally substituted heteromonocyclic group containing two nitrogen atoms as hetero atoms, and which may also contain one oxygen or sulfur atom, or pharmaceutically acceptable salt thereof.

The object compound (I) of the present invention can be prepared by the following processes.

Process 1

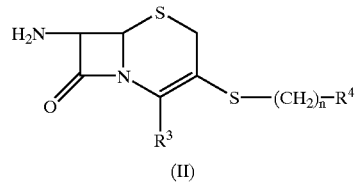

(II)

or its reactive derivative at the amino group, or a salt thereof

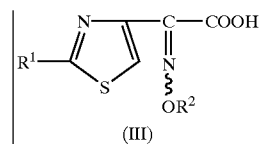

(III)

or its reactive derivative at the carboxy group, or a salt thereof

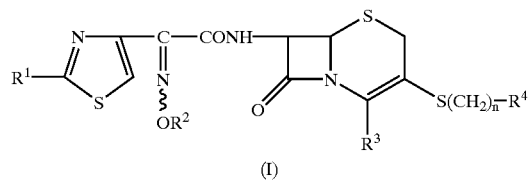

(I)

or a salt thereof

Process (2)

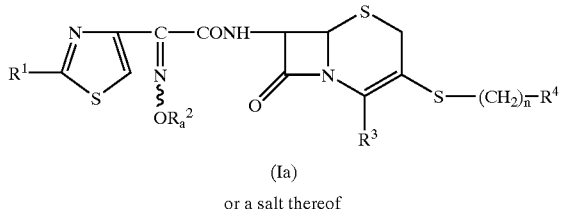

(Ia)

or a salt thereof elimination reaction of the hydroxy protective group

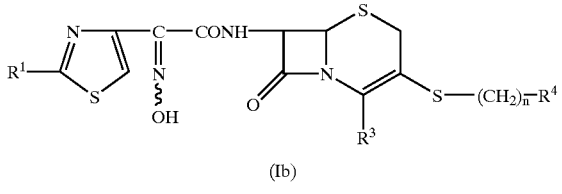

(Ib)

or a salt thereof

Process (3)

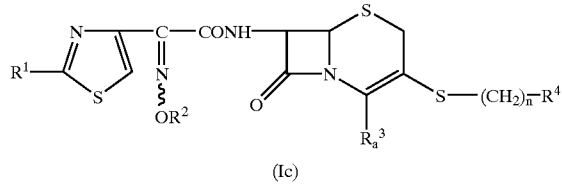

(Ic)

or a salt thereof elimination reaction of the carboxy protective group

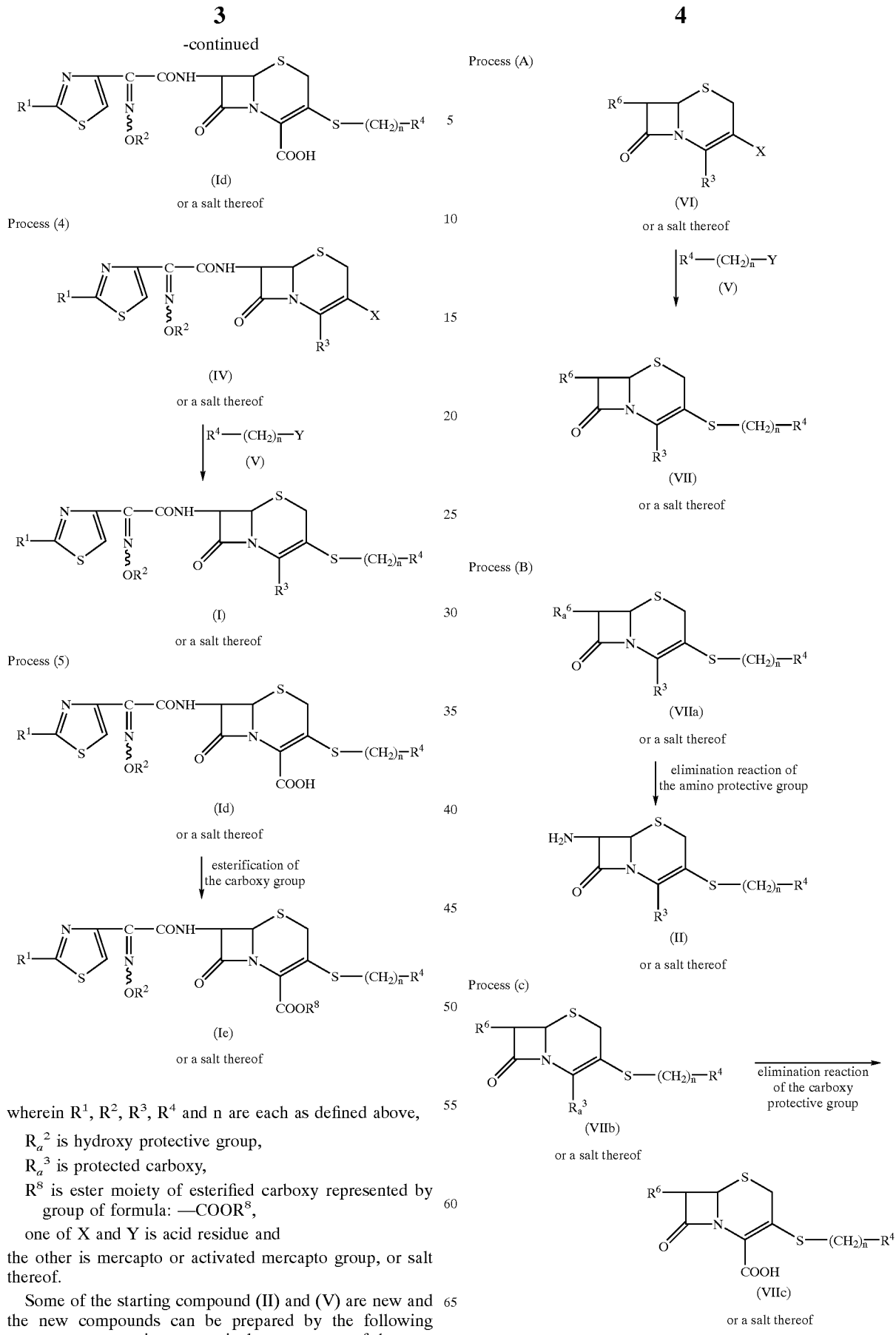

wherein $R^1$, $R^2$, $R^3$, $R^4$ and n are each as defined above, $R_a^2$ is hydroxy protective group, $R_a^3$ is protected carboxy, $R^8$ is ester moiety of esterified carboxy represented by group of formula: —COOR$^8$, one of X and Y is acid residue and the other is mercapto or activated mercapto group, or salt thereof.

Some of the starting compound (II) and (V) are new and the new compounds can be prepared by the following processes, preparations or equivalent processes of those.

Process (D)

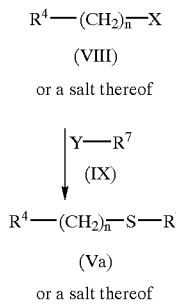

R⁴—(CH₂)ₙ—X (VIII)

or a salt thereof

↓ Y—R⁷ (IX)

R⁴—(CH₂)ₙ—S—R⁷

(Va)

or a salt thereof wherein R³, R_a³, R⁴, n, X and Y are each as defined above,
R⁶ is amino or protected amino,
R_a⁶ is protected amino and
R⁷ is acyl.

Regarding the compounds (I), (Ia), (Ib), (Ic), (Id), (Ie), (III) and (IV), it is to be understood that said compounds include syn isomer(Z), anti isomer(E) and a mixture thereof.

For example, with regard to the object compound (I), syn isomer(Z) means one geometrical isomer having the partial structure represented by the following formula:

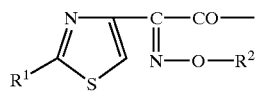

(wherein R¹ and R² are each as defined above), and anti isomer(E) means the other geometrical isomer having the partial structure represented by the following formula:

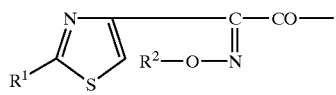

(wherein R¹, R² and Z are each as defined above), and all of such geometrical isomers and mixture thereof are included within the scope of this invention.

In the present specification and claim, the partial structure of these geometrical isomers and mixture thereof are represented for convenient sake by the following formula:

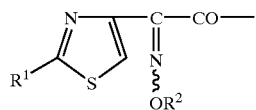

(wherein R¹, R² and Z are each as defined above).

It is to be noted that the compound (I) and the other compounds may include one or more stereoisomers due to asymmetric carbon atom(s), and all of such isomers and mixture thereof are included within the scope of this invention.

It is also to be noted that the solvate of the compound (I) [e.g. hydrate, lower alcohol solvate (e.g. methanol solvate, ethanol solvate, isopropanol solvate, etc), etc.] and any form of the crystal of the compound (I) are included within the present invention.

In the above and subsequent descriptions of the present specification, suitable examples and illustrations of the various definitions, which the present invention include within the scope thereof, are explained in detail as follows.

The term "lower" is intended to mean 1 to 6 carbon atom(s) unless otherwise indicated.

Suitable "lower alkyl" may include straight or branched one such as methyl, ethyl, propyl, isopropyl, butyl, t-butyl, pentyl, hexyl, and the like, in which more preferred one may be $C_1$–$C_4$ alkyl and the most preferred one may be methyl, ethyl or propyl.

Suitable "protected amino" group may include an amino group substituted by a conventional amino protective group which is easily removable such as acyl as defined below, such as organic silyl group which may have suitable substituent(s) (e.g., mono-, di- or tri(lower)alkylsilyl, etc.), such as ar(lower)alkyl which may have suitable substituent(s) (e.g. benzyl, trityl, p-nitrobenzyl, etc.) or the like.

Suitable "acyl" may include carbamoyl, aliphatic acyl group and acyl group containing an aromatic or heterocyclic ring. The aliphatic acyl may include saturated or unsaturated, acyclic or cyclic ones, such as alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.) and the like. The acyl group containing aromatic or heterocyclic ring may include arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have suitable substituent(s) such as halogen (e.g. chlorine, bromine, iodine or fluorine), lower alkyl as defined above, or the like.

Suitable "protected carboxy" may include an esterified carboxy and the like. Suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.); mono(or di or tri)halo(lower)alkyl ester (e.g. 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 1-propionyloxyethyl ester, etc.); cyclo(lower)alkylcarbonyloxy(lower)alkyl ester (e.g., 1-(cyclohexylcarbonyloxy)ethyl ester, etc.); lower alkoxycarbonyloxy(lower)alkyl ester (e.g., methoxycarbonyloxymethyl ester, ethoxycarbonyloxymethyl ester, propoxycarbonyloxymethyl ester, 1-(or 2-)[methoxycarbonyloxy]ethyl ester, 1-(or 2-)[ethoxycarbonyloxy]ethyl ester, 1-(or 2-)[propoxycarbonyloxy]ethyl ester, 1-(or 2-)[isopropoxycarbonyloxy]ethyl ester, etc.); cyclo(lower)alkyloxycarbonyloxy(lower)alkyl ester (e.g., 1-(cyclohexyloxycarbonyloxy)ethyl ester, etc.); lower alkanesulfonyl(lower)alkyl ester (e.g. mesylmethyl ester, 2-mesylethyl ester etc.); ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Suitable "hydroxy protective group" may include a conventional one which is easily removable such as acyl as mentioned above, cyclo(lower)alkenyl (preferable example of cyclo(lower)alkenyl is cyclo(C3–8)alkenyl such as cyclopentenyl or cyclohexenyl, etc.), phenyl(lower)alkyl which may have one or more suitable substituent(s) (e.g., benzyl, 4-methoxybenzyl, trityl, etc.), substituted silyl (e.g., trimethylsilyl, t-butyldimethylsilyl, etc.), tetrahydropyranyl and the like.

Suitable "aryl" may include phenyl, naphthyl and the like.

Suitable "heteromonocyclic group containing two nitrogen atoms as hetero atoms, which may also contain one or more oxygen or sulfur atoms" may include saturated or unsaturated, aromatic or non-aromatic 3 to 8-membered heteromonocyclic group containing two nitrogen atoms which may have one or more substituents. The heteromonocyclic group for $R^4$ can be attached to the adjacent partial structure-$(CH_2)_n$ at the carbon atom or the hetero atom in the heteromonocyclic ring, more preferably attached to the adjacent partial structure-$(CH_2)_n$ at the carbon atom in the heteromonocyclic ring.

Preferable example of heteromonocyclic group is (1) 5, 6 or 7 membered unsaturated heteromonocyclic ring containing 2 nitrogen atoms as hetero atoms such as pyrazole, pyrazoline, imidazole, imidazoline, pyrimidine or its partially hydrogenated compound, pyridazine or its partially hydrogenated compound, pyrazine or its partially hydrogenated compound, (2) 5, 6 or 7 membered heteromonocyclic ring containing 2 nitrogen atoms and more than 1 sulfur atom as hetero atoms such as 1,2,5-thiadiazole, 1,2,4-thiadiazole, 1,2,3-thiadiazole, 6H-1,2,5-thiadiazine or their hydrogenated compound, (3) 5, 6 or 7 membered heteromonocyclic ring containing 2 nitrogen atoms and more than 1 oxygen atom as hetero atoms as hetero atoms such as 1,2,3-oxadiazole, 1,2,5-oxadiazole 1,2,4-oxadiazole, 6H-1,2,5-oxadiazine or their hydrogenated compounds.

(4) saturated 5, 6 or 7 membered heteromonocyclic ring containing 2 nitrogen atoms as hetero atoms such as pyrazolidine, imidazolidine, piperazine, 1,3-diazacyclohexane, 1,2-diazacyclohexane.

The heteromonocyclic group for may have one to four, same and different, suitable substituent(s) such as lower alkyl as exemplified before; lower alkoxy (e.g. methoxy, ethoxy, propoxy, etc.); lower alkylthio (e.g. methylthio, ethylthio, etc.); lower alkylamino (e.g. methylamino, ethylamino, etc.); cyclo(lower)alkyl (e.g. cyclopentyl, cyclohexyl, etc.); cyclo(lower)alkenyl (e.g. cyclohexeny, cyclohexadienyl, etc.); halogen; amino; protected amino as exemplified before; protected hydroxy which has a hydroxy protective group as exemplified before; cyano; nitro; carboxy; hydroxy(lower)alkyl (e.g. hydroxymethyl, 2-hydroxyethyl, etc.); amino(lower)alkyl (e.g. aminomethyl, aminoethyl, etc.); carbamoyloxy; and the like.

More preferable "optionally substituted heteromonocyclic group containing two nitrogen atoms as hetero atoms, which may also contain one oxygen or sulfur atom" may include 5 or 6 membered, 4-methyl-1,2,3-thiadiazol-5-yl, pyrazol-4-yl, 1-methylpyrazol-4-yl, 1,2,5-thiadiazol-3-yl, 2-methyl-1,3,4-thiadiazol-5-yl, 3-methyl-1,2,4-thiaziazol-5-yl, imidazol-2-yl, 2-methyl-1,3,4-oxadiazol-5-yl, pyradin-2-yl, pyrimidin-4-yl, pyridazin-3-yl, 1,2,3-thiadiazol-4-yl, 1,2,3-thiadiazol-5-yl and the like.

Suitable "acid residue" may include halogen (e.g., fluorine, chlorine, bromine, iodine, etc.), acyloxy in which the acyl moiety can be referred to one as aforementioned and the like. More preferable acyloxy is sulfonyloxy (e.g., methanesulfonyloxy, benzenesulfonyloxy, tosyloxy, etc.), lower alkanoyloxy (e.g., acetyloxy, propionyloxy, etc.), etc.

Suitable salt of mercapto group or activated mercapto group of the compound (V) may include a metal salt such as an alkali metal salt (e.g., sodium salt, potassium salt, etc.) an alkaline earth metal salt (e.g., magnesium salt, etc.), aluminum salt, an acylated thiol and the like.

Suitable "acyl moiety" in the term "acylated thiol" may include aliphatic acyl group and acyl group containing an aromatic or heterocyclic ring. And suitable examples of the said acyl may be lower alkanoyl (e.g. formyl, acetyl, propionyl, butyryl, isobutyryl, valeryl, isovaleryl, oxalyl, succinyl, pivaloyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have suitable substituent(s) such as halogen (e.g. chloride, bromine, iodine or fluorine), lower alkyl as defined above, or the like.

Suitable pharmaceutically acceptable salts of the object compound (I) are conventional non-toxic pharmaceutically acceptable salts and include a salt with a base or an acid addition salt, for example an inorganic base salt [a metal salt such as an alkali metal salt (e.g. sodium salt, potassium salt, etc.) and an alkaline earth metal salt (e.g. calcium salt, magnesium salt, etc.), an ammonium salt etc.], an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, aspartic acid salt, glutamic acid salt, etc.], and the like.

The processes for preparing the object and starting compounds of the present invention are explained in detail in the following.

Process (1)

The compound (I) or a salt thereof can be prepared by reacting the compound (II) or its reactive derivative at the amino group, or a salt thereof with the compound (III) or its reactive derivative at the carboxy group, or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl) acetamide [e.g. N-(trimethylsilyl)acetamide], bis(trimethylsilyl)urea or the like; a derivative formed by reaction of the compound (II) with phosphorus trichloride or phosgene and the like.

Suitable reactive derivative at the carboxy group of the compound (III) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, 1-hydroxy-1H-benzotriazole, dimethylpyrazole, triazole or tetrazole; or an activated ester [e.g. cyanomethyl ester, methoxymethyl ester, dimethyliminomethyl [$(CH_3)_2{}^+N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N'-carbonyl-bis(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, diisopropylethylamine, etc.), pyridine, N-(lower) alkylmorpholine, N,N-di(lower)alkylbenzylamine, or the like.

The reaction temperature is not critical, and the reaction is usually carried out under cooling to warming.

Process (2)

The compound (Ib) or a salt thereof can be prepared by subjecting the compound (Ia) or a salt thereof to elimination reaction of the hydroxy protective group. Suitable method of this elimination reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an metal hydroxide [e.g. sodium hydroxide, magnesium hydroxide, etc.], metal alkoxide [e.g. sodium methoxide, potassium methoxide, etc.], metal carbonate or metal bicarbonate, trialkylamine [e.g. trimethylamine, triethylamine, etc.], picoline, 1,5-diazabicyclo[4.3.0]-non-5-ene, 1,4-diazabicyclo[2.2.2] octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, ammonium chloride, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, dioxane, tetrahydrofuran, N,N-dimethylformamide, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

The present invention includes, within the scope of the invention, the case that the protected amino group in $R^1$ and/or the protected carboxy group in $R^3$ are/is transformed into an amino group and/or a carboxy group during this reaction respectively.

Process (3)

The compound (Id) or a salt thereof can be prepared by subjecting the compound (Ic) or a salt thereof to elimination reaction of the carboxy protective group.

This reaction can be carried out in a similar manner to that of the aforementioned Process (2), and therefore the reagents to be used and the reaction conditions (e.g., solvent, reaction temperature, etc.) can be referred to those of the Process (2).

The present invention includes, within the scope of the invention, the case that the protected amino group in $R^1$ and/or the hydroxy protective group in $R^2$ are/is transformed into an amino group and/or a hydrogen during this reaction.

Process (4)

The object compound (I) or a salt thereof can be prepared by reacting a compound (IV) or a salt thereof with a compound (V) or a salt thereof.

The reaction is preferably carried out in the presence of a base, for example, an organic or an inorganic base such as alkali metal hydroxide, alkali metal carbonate, alkali metal bicarbonate, alkali metal alkoxide (e.g., sodium methoxide, sodium ethoxide, etc.), N,N-diisopropylethylamine, pyridine or the like, and preferably carried out around neutral conditions. The reaction temperature is not critical and the reaction is usually carried out under cooling, at ambient temperature or under warming.

Process (5)

The compound (Ie) or a salt thereof can be prepared by subjecting the compound (Id) or a salt thereof to esterification reaction.

Suitable esterifying agent to be used in this reaction may include a conventional one such as an alcohol of formula: HO—$R^8$ (X)(wherein $R^8$ is as defined above) or its reactive equivalent (e.g., halide, sulfonate, sulfate, diazo compound, etc.) or a salt thereof, or the like.

This reaction is usually carried out in the presence of a base.

Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.) alkali metal carbonate (e.g., sodium carbonate, potassium carbonate, cesium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkali earth metal phosphate (e.g., magnesium phosphate, calcium phosphate, etc.), alkali metal hydrogen phosphate (e.g., disodium hydrogen phosphate, dipotassium hydrogen phosphate, etc.) or the like, and an organic base such as trialkylamine (e.g., trimethylamine, triethylamine, etc.), picoline, N-methylpyrrollidine, N-methylmorpholine, 1,5-diazabicyclo[4.3.0]non-5-ene, 1,4-diazabicyclo[2.2.2]octane, 1,5-diazabicyclo[5.4.0]undecene-5 or the like.

This reaction is usually carried out in a solvent such as benzene, N,N-dimethylformamide, tetrahydrofuran, toluene, methylene chloride, ethylene dichloride, chloroform or any other solvent which does not adversely affect the reaction.

The reaction temperature is not critical and the reaction is usually carried out under cooling to heating.

The compound (X) or its reactive equivalent, or a salt thereof can be prepared in the manner disclosed in Preparations, similar manners thereto or a conventional manner.

Process (A)

The compound (VII) or a salt thereof can be prepared by reacting a compound (V) or a salt thereof with a compound (VI) or a salt thereof.

This reaction can be carried out in a similar manner to that of the aforementioned Process (4), and therefore the reagents to be used and the reaction conditions (e.g., solvent, reaction temperature, etc.) can be referred to those of the Process (4).

Process (B)

The compound (II) or a salt thereof can be prepared by subjecting the compound (VIIa) or a salt thereof to an elimination reaction of the amino protective group.

This reaction can be carried out in a similar manner to that of the aforementioned Process (2), and therefore the reagents to be used and the reaction conditions (e.g., solvent, reaction temperature, etc.) can be referred to those of the Process (2).

The present invention includes, within the scope of the invention, the case that the protected carboxy group in $R^3$ is transformed into a carboxy group during this reaction.

Process (C)

The compound (VIIc) or a salt thereof can be prepared by subjecting the compound (VIIb) or a salt thereof to an elimination reaction of the carboxy protective group.

This reaction can be carried out in a similar manner to that of the aforementioned Process (3) and therefore the reagents to be used and the reaction conditions (e.g., solvent, reaction temperature, etc.) can be referred to those of the Process (3).

Process (D)

The compound (Va) or a salt thereof can be prepared by subjecting the compound (VIII) or a salt thereof with a compound (IX) or a salt thereof.

This reaction can be carried out in a similar manner to that of the aforementioned Process (4) and therefore the reagents to be used and the reaction conditions (e.g., solvent, reaction temperature, etc.) can be referred to those of Process (4).

Suitable salts of the object and starting compounds and their reactive derivatives in Processes (1)–(4) and (A)–(D) can be referred to the ones as exemplified for the compound (I).

The object compound (I) and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on MIC (minimal inhibitory concentration) of representative compound of this invention are shown in the following.

(A) Minimal Inhibitory Concentration

Test Method:

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar)containing graded concentrations of representative test compound, and the minimal inhibitory concentration (MIC) was expressed in terms of µg/ml after incubation at 37° C. for 20 hours.

Test Compound:
(1) 7β-[2-(2-Aminothiazol-4-yl)-2-(Z)-(hydroxyimino) acetamido]-3-[(4-pyridyl)methylthio]-3-cephem-4-carboxylic acid.
(2) 7β-[2-(2-Aminothiazol-4-yl)-2-(Z)-(hydroxyimino) acetamido]-3-[(4-methyl-1,2,3-thiadiazol-5-yl) methylthio]-3-cephem-4-carboxylic acid.
(3) 7β-[2-(2-Aminothiazol-4-yl)-2-(Z)-(hydroxyimino) acetamido]-3-[(pyrazol-4-yl)methylthio]-3-cephem-4-carboxylic acid.

Test result:

| Test strain | Test compound | | |
|---|---|---|---|
| | (1) | (2) | (3) |
| S. aureus | 0.143 | 0.167 | 0.23 |
| E. coli | 0.061 | 0.072 | 0.033 |
| H. influenzae | 0.067 | 0.118 | 0.129 |

(B) Urinary Excretion

Test Method

Male JCL SD strain rats (age, 6–7 weeks) were used. Test compound was suspended in 0.5% methyl cellulose solution. The rats were starved overnight before dosing with 20 mg/kg. Urine samples were collected at 0 to 6 and 6 to 24 hours after oral administration were measured by the disc-plate diffusion method using Bacillus subtilis ATCC 6633 as test organism and sodium citrate agar (0.8% sodium citrate, 0.5% polypeptone, 0.3% beef extract and 1.0% agar) as the test medium. The plate were incubated at 37° C. for 18 hours and the zone of inhibition were measured.

Test Compound
(3) 7β-[2-(2-Aminothiazol-4-yl)-2-(Z)-(hydroxyimino) acetamido]-3-[(pyrazol-4-yl)methylthio]-3-cephem-4-carboxylic acid.

Test Result

| Test compound | Urinary recovery in 24 hours (%) |
|---|---|
| (3) | 50.0 |

For therapeutic administration, the object compound (I) and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration.

The pharmaceutical preparations may be in solid form such as tablet, granule, powder, capsule, or liquid form such as solution, suspension, syrup, emulsion, lemonade and the like.

In needed, there may be included in the above preparations, auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary and depend upon the age, conditions of the patient, a kind of diseases, a kind of the compound (I) to be applied, etc. In general, amounts between 1 mg and about 4,000 mg or even more per day may be administered to a patient. An average single dose of about 10 mg, 50 mg, 100 mg, 250 mg, 500 mg, 1000 mg of the object compound (I) of the present invention may be used in treating diseases infected by pathogenic microorganisms.

Preferred embodiments of the object compound (I) are as follows.

$R^1$ is amino, or amino group which is substituted by an easily removable protective group, $R^2$ is hydrogen, lower alkyl or easily removable protective group, $R^3$ is carboxy or esterified carboxy, $R^4$ is 3 to 8-membered heteromonocyclic group containing two nitrogen atoms which may have one or more substituents consisting from lower alkyl, hydroxy (lower)alkyl and amino(lower)alkyl one or more lower alkyl, and n is 1 or 2.

The following Preparations and Examples are given for the purpose of illustrating the present invention in more detail.

Abbreviation used in the Preparations and Examples mean as follows.

THF: tetrahydrofuran
IPA: isopropyl alcohol,
IPE: diisopropyl ether,
DMF: N,N-dimethylformamide and
HP-20: trademark of macroporus resin.

PREPARATION 1

To a solution of diphenylmethyl 7β-formamido-3-methanesulfonyloxy-3-cephem-4-carboxylate (14.66 g, 30 m mol) in DMF (103 ml) was added 4-(mercaptomethyl) pyridine (4.13 g, 33 m mol) at −20° C., followed by dropwise addition of N,N-diisopropylethylamine (3.88 g, 30 m mol). The mixture was stirred at the same temperature for 1.9 hours and poured into ice water (500 ml). The resulting precipitates were collected by filtration and washed with water. The powder was dissolved in THF, and ethyl acetate and water were added respective. The separated organic layer was washed with brine, dried over magnesium sulfate and evaporated in vacuo. The residue was purified by column chromatography on silica gel to give diphenylmethyl 7β-formamido-3-[(4-pyridyl)methylthio]-3-cephem-4-carboxylate (13.73 g).

IR (Nujol): 1750, 1660, 1590 cm$^{-1}$; NMR (DMSO-d$_6$, δ): 3.82 (2H, br s), 4.19 (2H, br s), 5.18 (1H, d, J=4.7 Hz), 5.77 (1H, dd, J=8.9 and 4.7 Hz), 6.87 (1H, s), 7.3–7.6 (12H, m), 8.17 (1H, s), 8.45–8.55 (2H, m), 9.12 (1H, d, J=8.9 Hz).

PREPARATION 2

To a solution of diphenylmethyl 7β-formamido-3-[(4-pyridyl)methylthio]-3-cephem-4-carboxylate (13.70 g, 26.5 m mol) in methanol (65 ml) was added dropwise conc. HCl (11.0 ml) at room temperature and the mixture was stirred at the same temperature for 2.8 hours. The mixture was poured into a mixture of ethyl acetate and ice water and adjusted to pH 7 by addition of 5N NaOH aq. The separated organic layer was washed with water and brine, dried over magnesium sulfate and evaporated in vacuo. The residue was triturated with ethyl acetate to give diphenylmethyl 7β-amino-3-[(4-pyridyl)methylthio]-3-cephem-4-carboxylate (5.16 g).

IR (Nujol): 1755, 1720, 1595 cm$^{-1}$; NMR (DMSO-d$_6$, δ): 2.37 (2H, br s), 3.73 and 3.83 (2H, ABq, J=17.6 Hz), 4.11 (2H, s), 4.79 (1H, d, J=5.0 Hz), 5.00 (1H, d, J=5.0 Hz), 6.85 (1H, s), 7.2–7.5 (12H, m), 8.48 (2H, dd, J=4.4 and 1.6 Hz).

PREPARATION 3

The following compounds were obtained according to a similar manner to that of Preparation 1.

(1) Diphenylmethyl 7β-formamido-3-[(1,2,3-thiadiazol-4-yl)methylthio]-3-cephem-4-carboxylate IR (Nujol): 1760, 1680, 1645, 1555 cm$^{-1}$; NMR (DMSO-d$_6$, δ): 3.99 (2H, s), 4.69 (2H, s), 5.20 (1H, d, J=4.7 Hz), 5.77 (1H, d, J=9.3 and 4.7 Hz), 6.83 (1H, s), 7.2–7.5 (10H, m), 8.18 (1H, s), 9.02 (1H, s), 9.14 (1H, d, J=9.3 Hz).

(2) Diphenylmethyl 7β-formamido-3-[(pyrazin-2-yl)methylthio]-3-cephem-4-carboxylate IR (KBr): 1782, 1691 cm$^{-1}$; NMR (DMSO-d$_6$, δ): 3.96 (2H, s), 4.36 (2H, s), 5.19 (1H, d, J=5 Hz), 5.77 (1H, dd, J=5 and 9 Hz), 6.83 (1H, s), 7.2–7.5 (10H, m), 8.18 (1H, s), 8.5–8.7 (3H, m), 9.14 (1H, d, J=9 Hz).

PREPARATION 4

The following compounds were obtained according to a similar manner to that of Preparation 2.

(1) Diphenylmethyl 7β-amino-3-[(1,2,3-thiadiazol-4-yl)methylthio]-3-cephem-4-carboxylate IR (Nujol): 1760 cm$^{-1}$; NMR (DMSO-d$_6$, δ): 2.41 (2H, br s), 3.95 (2H, br s), 4.59 and 4.66 (2H, ABq, J=14.3 Hz), 4.81 (1H, d, J=5.0 Hz), 5.03 (1H, d, J=5.0 Hz), 6.81 (1H, s), 7.2–7.5 (10H, m), 8.99 (1H, s).

(2) Diphenylmethyl 7β-amino-3-[(pyrazin-2-yl)methylthio]-3-cephem-4-carboxylate

IR (KBr): 1774 cm$^{-1}$; NMR (DMSO-d$_6$, δ): 2.44 (2H, br s), 3.92 (2H, s), 4.28 (2H, s), 4.80 (1H, d, J=5 Hz), 5.02 (1H, d, J=5 Hz), 6.80 (1H, s), 7.2–7.5 (10H, m), 8.5–8.6 (3H, m).

PREPARATION 5

To a solution of diphenylmethyl 7β-amino-3-[(1,2,3-thiadiazol-4-yl)methylthio]-3-cephem-4-carboxylate (4.68 g, 9.42 m mol) in formic acid (18.7 ml) was added conc. HCl (3.93 ml) at room temperature and the mixture was stirred at the same temperature for 1.5 hours. The mixture was poured into a cooled mixture of acetone (140 ml) and ethyl acetate (280 ml) and the precipitates were collected by filtration, washed with acetone and dried in vacuo to give 7β-amino-3-[(1,2,3-thiadiazol-4-yl)methylthio]-3-cephem-4-carboxylic acid hydrochloride (2.63 g).

IR (Nujol): 1770, 1680 cm$^{-1}$; NMR (DMSO-d$_6$, δ): 3.95 (2H, s), 4.74 (2H, s), 5.02 (1H, d, J=4.7 Hz), 5.19 (1H, d, J=4.7 Hz), 9.13 (1H, s).

PREPARATION 6

The following compound was obtained according to a similar manner to that of Preparation 5.

(1) 7β-Amino-3-[(pyrazin-2-yl)methylthio]-3-cephem-4-carboxylic acid hydrochloride IR (KBr): 1780, 1772 cm$^{-1}$; NMR (DMSO-d$_6$, δ): 3.92 (2H, s), 4.36 and 4.45 (2H, ABq, J=14 Hz), 5.02 (1H, d, J=5 Hz), 5.18 (1H, d, J=5 Hz), 8.5–8.6 (3H, m).

PREPARATION 7

Under N$_2$ atmosphere, potassium tert-butoxide (9.60 g, 85.5 m mol) and trityl chloride (21.9 g, 78.5 m mol) were added successively to a solution of 4-(ethoxycarbonyl) pyrazole (10.0 g, 71.3 m mol) in DMF (100 ml) at 0° C. After stirred for 1 hour, the mixture was poured into water/ ethyl acetate. The aqueous layer was separated, and the organic layer was washed with water, brine and dried over magnesium sulfate. After evaporation of the solvent, the resulting precipitate was recrystallized from ethyl acetate to afford 4-ethoxycarbonyl-1-(trityl)pyrazole (21.7 g).

NMR (CDCl$_3$, δ): 1.30 (3H, t, J=7.12 Hz), 4.25 (2H, q, J=7.12 Hz), 7.06–7.40 (15H, m), 7.93 (1H, s), 8.04 (1H, s).

PREPARATION 8

2.7 g of sodium borohydride (70.9 m mol) was added portionwise to a solution of 12.5 g of 5-ethoxycarbonyl-4-methyl-1,2,3-thiadiazole in ethanol (90 ml) at room temperature. Stirring was continued for 1 hour, the mixture was poured into water/ethyl acetate, and the aqueous layer was separated. The organic layer was washed with water and brine, dried over magnesium sulfate. After filtration, the filtrate was concentrated in vacuo, to afford 5-hydroxymethyl-4-methyl-1,2,3-thiadiazole (3.32 g).

NMR (CDCl$_3$, δ): 2.63 (3H, s), 5.01 (2H, s).

PREPARATION 9

The following compounds were obtained according to a similar manner to that of Preparation 8.

(1) 5-Hydroxymethyl-1,2,3-thiadiazol

NMR (CDCl$_3$, δ): 3.18 (1H, br, s), 5.15 (2H, s), 8.62 (1H, s).

(2) 4-Hydroxymethyl-1-(trityl)pyrazole

NMR (CDCl$_3$, δ): 4.52 (2H, s), 7.05–7.35 (15H, m), 7.37 (1H, s), 7.65 (1H, s).

PREPARATION 10

Under nitrogen atmosphere, 10.0 ml of triethylamine (72.6 m mol) and 4.1 ml of methanesulfonyl chloride (53 m mol) was added successively to a solution of 6.27 g of 5-hydroxymethyl-4-methyl-1,2,3-thiadiazole (48.16 m mol) in dichloromethane (50 ml) at −30° C. After stirring for 30 minutes, the mixture was poured into water-dichloromethane while the pH was kept between 8.5–9.0. The aqueous layer was separated, the organic layer was washed with saturated sodium hydrocarbonate, washed with dil-hydrochloric acid brine, dried over magnesium sulfate. After filtration, the filtrate was concentrated in vacuo to afford 5-methanesulfonyloxymethyl-4-methyl-1,2,3-thiadiazol (9.8 g).

NMR (CDCl$_3$, δ): 2.76 (3H, s), 3.06 (3H, s), 5.51 (2H, s).

PREPARATION 11

The following compounds were obtained according to a similar manner to that of Preparation 10.

(1) 5-Methanesulfonyloxymethyl-1,2,3-thiadiazole

NMR (CDCl$_3$, δ): 3.09 (3H, s), 5.63 (2H, s), 8.76 (1H, s).

(2) 1-Trityl-4-(methanesulfonyloxymethyl)-pyrazole

NMR (CDCl$_3$, δ): 2.92 (3H, s), 4.46 (2H, s), 7.05–7.50 (5H, m), 7.42 (1H, s), 7.65 (1H, s).

PREPARATION 12

Under nitrogen atmosphere, 6.64 ml (56.5 m mol) of thiobenzoic acid was added to a stirred solution of potassium tert-butoxide (6.07 g, 54.1 m mol) in DMF (80 ml) at 0° C. After stirring for 10 minutes, 5-methanesulfonyloxymethyl-4-methyl-1,2,3-thiadiazole (9.8 g, 47.0 m mol) in DMF (30 ml) was added to the mixture slowly at the same temperature. The whole mixture was stirred at 80° C. for 2 hours, poured into a mixture of diluted aqueous sodium hydrogen carbonate and ethyl acetate. Aqueous layer was separated, the organic layer was washed with brine, and dried over magnesium sulfate. After evaporation of the solvent, the residue was treated on silica gel (eluent: n-hexane/ethyl acetate=9/1–8/2) to afford 5-benzoylthiomethyl-4-methyl-1,2,3-thiadiazole (7.51 g).

NMR (CDCl$_3$, δ): 2.73 (3H, s), 4.47 (2H, s), 7.42–7.65 (3H, m), 7.90–7.97 (2H, m).

PREPARATION 13

The following compounds were obtained according to a similar manner to that of Preparation 12.
(1) 5-Benzoylthiomethyl-1,2,3-thiadiazole
  NMR (CDCl$_3$, δ): 4.61 (2H, s), 7.44–7.67 (3H, m), 7.92–7.98 (2H, m), 8.68 (1H, s).
(2) 4-Benzoylthiomethyl-1-(trityl)pyrazole
  NMR (CDCl$_3$, δ): 4.15 (2H, s), 7.05–7.65 (20H, m), 7.90–8.00 (2H, m).

PREPARATION 14

Under nitrogen atmosphere, 78.7 g of triphenylphosphine (300 m mol) and 47.2 ml of diethyl azodicarboxylate (300 m mol) were added to a stirred solution of 22.4 g of 4-hydroxymethyl-1-methylpyrazole (200 m mol) in THF (250 ml) at 5° C. After stirring for 1 hour at the same temperature, 42.3 ml of thiobenzoic acid (360 m mol) was added slowly to the mixture. The mixture was poured into a mixture of water and ethyl acetate, while Ph was adjusted to 9.5 with 30% potassium bicarbonate. Aqueous layer was separated, the organic layer was washed with brine, dried over magnesium sulfate. After filtration of the mixture, the filtrate was concentrated in vacuo, and the residue was purified on silica gel (eluent: n-hexane-ethyl acetate) to afford 4-(benzoylthiomethyl)-1-methylpyrazole (18.3 g).

NMR (CDCl$_3$, δ): 3.84 (3H, s), 4.14 (2H, s), 7.27–7.62 (5H, m), 7.92–7.98 (2H, m).

PREPARATION 15

The following compounds were obtained according to a similar manner to that of Preparation 14.
(1) 3-(Benzoylthiomethyl)pyridazine
  IR (KBr): 1660 cm$^{-1}$; NMR (DMSO-d$_6$, δ): 4.65 (2H, s), 7.5–7.9 (5H, m), 7.9–8.0 (2H, m), 9.1–9.2 (1H, m).
(2) 3-Benzoylthiomethyl-1,2,5-thiadiazole
  NMR (CDCl$_3$, δ): 4.58 (2H, s), 7.40–7.70 (3H, m), 7.90–8.00 (2H, m), 8.61 (1H, s).

PREPARATION 16

A solution of 3-(benzoylthiomethyl)pyridazine (10.6 g, 46.0 m mol) in acetonitrile (53 ml) was added 28% sodium methylate in methanol (9.6 ml, 46.0 m mol) at 5° C. The mixture was stirred at 5° C. for 30 minutes. The reaction mixture was evaporated in vacuo. The residue was poured into a mixture of ethyl acetate and ice-water. The aqueous layer was separated, adjusted to pH 7 by addition of 1N HCl and extracted with ethyl acetate. The organic layer was separated, washed with brine, dried over MgSO$_4$, and evaporated in vacuo to give 3-(mercaptomethyl)pyridazine (938 mg).

IR (Film): 2540 cm$^{-1}$; NMR (DMSO-d$_6$, δ): 3.19 (1H, t, J=8 Hz), 4.00 (2H, d, J=8 Hz), 7.4–7.8 (2H, m), 9.1–9.2 (1H, m).

PREPARATION 17

Suspension A; 4-Chloromethyl-1-tritylpyrazole (198.3 g) was suspended in acetone (3.0 l) and it was warmed at 50° C. After it was dissolved, sodium iodide (165.6 g) was added to the solution at the room temperature. The solution was stirred at the same temperature for an hour, and then it was poured into a mixture of ethyl acetate (3.0 l) and water (3.0 l). The organic layer was separated and dried over magnesium sulfate, was evaporated. The residue was suspended in DMF (400 ml) to give suspension A.

Suspension B; On the other hand, under N$_2$ atmosphere 70% sodium hydrosulfide (36.1 g) was suspended in DMF (0.6 l) at the room temperature, N,N-diisopropylethylamine (107 ml) was added to the suspension to give suspension B.

The solution of diphenylmethyl 7β-formamido-3-methanesulfonyloxy-3-cephem-4-carboxylate (200 g) in DMF (1.6 l) was cooled below −2° C., suspension B was dropped into the solution below 0° C. for 40 minutes. After stirring at the same temperature for one hour, the suspension A was dropped into the solution below 0° C., and stirred at the same temperature for 30 minutes. The reaction mixture was poured into a mixture of ethyl acetate (7 l) and water (7 l), aqueous layer was adjusted to pH 6.5 with 3N-hydrochloric acid. Organic layer was separated, washed with water (4 l). The organic layer was left at 5° C. for 14 hours. The resulting precipitate was collected by filtration, washed with ethyl acetate (1.5 l) to give diphenylmethyl 7β-formamido-3-[(1-tritylpyrazol-4-yl)methylthio]-3-cephem-4-carboxylate (242 g) as powder.

IR (KBr): 1772, 1732, 1693, 1660, 1375, cm$^{-1}$; NMR (DMSO-d$_6$, δ): 3.81 (2H, s), 4.05 (2H, s), 5.12 (1H, d, J=4.6 Hz), 5.74 (1H, dd, J=4.6 Hz, J=8.7 Hz), 6.84 (1H, s), 7.00–7.56 (27H, m), 8.19 (1H, s), 9.12 (1H, d, J=8.7 Hz); FAB-Mass: 748 (M$^+$).

PREPARATION 18

The following compound was obtained according to a similar manner to that of Preparation 17.

Diphenylmethyl 7β-phenylacetamido-3-(1-tritylpyrazol-4-yl)methylthio-3-cephem-4-carboxylate IR (KBr): 1781, 1685, 1533, 1496 cm$^{-1}$; NMR (DMSO-d$_6$, δ): 3.51 and 3.61 (2H, ABq, J=18 Hz), 3.81 (2H, br s), 4.01 (2H, br s), 5.07 (1H, d, J=5 Hz), 5.65 (1H, dd, J=5 Hz, 7 Hz), 6.84 (1H, s), 7.00–7.60 (32H, m), 9.16 (1H, d, J=7 Hz).

PREPARATION 19

Under nitrogen atmosphere, the mixture of 440 mg of sodium hydrosulfide and 1.3 ml of diisopropylethylamine in DMF (10 ml) was added to a solution of diphenylmethyl 7β-formamido-3-methanesulfonyloxy-3-cephem-4-carboxylate (2.44 g) in DMF (15 ml) with dry ice-tetrachloromethane cooling. Stirring was continued for 30 minutes, 918 mg of 4-chloromethylpyrazole hydrochloride and 1.04 ml of diisopropylethylamine was added successively to the solution. The whole mixture was stirred for 1 hour, and then poured into a mixture of water and ethyl acetate. Organic layer was separated, and washed with diluted hydrochloric acid and brine, successively, and dried over magnesium sulfate. After evaporation of the solvent, the residue was purified on silica gel (eluent:

dichloromethane-acetone) to afford diphenylmethyl 7β-formamido-3-[(pyrazol-4-yl)-methylthio]-3-cephem-4-carboxylate (2.96 g).

IR (KBr): 3303.5, 1791.5, 1760.7, 1672.0, 1535.1 cm$^{-1}$; NMR (DMSO-d$_6$, δ): 3.88 (2H, s), 4.05, 4.09 (2H, ABq, J=13.2 Hz), 5.19 (1H, d, J=4.6 Hz), 5.74 (1H, dd, J=9.0 Hz, 4.6 Hz), 6.84 (1H, s), 7.20–7.80 (12H, m), 8.18 (1H, s), 9.12 (1H, d, J=9.4 Hz), 12.78 (1H, s).

PREPARATION 20

The following compound was obtained according to a similar manner to that of Preparation 19.

Diphenylmethyl 7β-phenylacetamido-3-[(pyrazol-4-yl)methylthio]-3-cephem-4-carboxylate IR (KBr): 1772, 1716, 1648, 1558, 1496 cm$^{-1}$; NMR (DMSO-d$_6$, δ): 3.51 and 3.60 (2H, ABq, J=18 Hz), 3.88 (2H, br s), 4.03 and 4.10 (2H, ABq, J=18 Hz), 5.15 (1H, d, J=5 Hz), 5.65 (1H, dd, J=5 Hz, 7 Hz), 6.84 (1H, s), 7.10–7.65 (17H, m), 9.18 (1H, d, J=7 Hz).

PREPARATION 21

To a solution of diphenylmethyl 7β-formamido-3-methanesulfonyloxy-3-cephem-4-carboxylate (1 g) in DMF (10 ml) was added sodium salt of 5-mercapto-1,2,3-thiadiazole (445 mg) at −30° C. After being stirred at −20° C. for 1 hour, the mixture was poured into a mixture of ice water and ethyl acetate. The organic layer was separated washed with water and brine, dried over magnesium sulfate, and evaporated to give diphenylmethyl 7β-formamido-3-[(1,2,3-thiadiazol-5-yl)thio]-3-cephem-4-carboxylate (961 mg).

IR (KBr): 1783.8, 1735.6, 1681.6 cm$^{-1}$; NMR (DMSO-d$_6$, δ): 3.58 and 3.86 (2H, ABq, J=17.8 Hz), 5.28 (1H, d, J=5.1 Hz), 5.96 (1H, dd, J=9.4 Hz, 5.1 Hz), 6.97 (1H, s), 7.26–7.39 (10H, m), 8.16 (1H, s), 8.86 (1H, s), 9.23 (1H, d, J=9.4 Hz).

PREPARATION 22

Diphenylmethyl 7β-formamido-3-[(1-tritylpyrazol-4-yl)methylthio]-3-cephem-4-carboxylate (121.7 g) was suspended in methanol (1.46 l), concentrated hydrochloric acid (94.8 ml) was added thereto below 25° C. The reaction mixture was stirred at the room temperature for 3 hours, and then concentrated hydrochloric acid (4.0 ml) was added. After the reaction mixture was stirred at the same temperature for one hour, insoluble precipitate was filtered off below 10° C. The filtrate was poured into a mixture of ethyl acetate (4.5 l) and water (4 l). The aqueous layer was adjusted at pH 4.0 with 30% aqueous sodium hydroxide solution and then was adjusted at pH 6.9 with 2N-potassium hydroxide. The organic layer was separated, washed with brine (4 l), dried over magnesium sulfate, and evaporated until the volume amounted to 700 ml. IPE (100 ml) was added to the suspension gradually below 10° C., and was left below 10° C. for 12 hours. The precipitate was filtered and dried under reduced pressure to give diphenylmethyl 7β-amino-3-[(pyrazol-4-yl)methylthio]-3-cephem-4-carboxylate (62.4 g) as powder.

IR (KBr): 1743, 1697, 1369, 1213 cm$^{-1}$; NMR (DMSO-d$_6$, δ): 2.34 (2H, s), 3.84 (2H, s), 4.01 (2H, s), 4.79 (1H, s), 5.02 (1H, d, J=4.9 Hz), 6.82 (1H, s), 7.24–7.59 (12H, m), 12.76 (1H, s); FAB-Mass: 479 (M$^+$+1); Elemental Analysis Calcd. for $C_{24}H_{22}N_4O_3S_2$; C, 60.23, H, 4.63, N, 11.71; Found: C, 60.33, H, 4.88, N, 11.63.

PREPARATION 23

Pyridine (1.3 ml) was added to a suspension of phosphorus pentachloride (3.37 g) in dichloromethane (47.6 ml) at −10° C., and the mixture was stirred at between −15 to −5° C. for 30 minutes. Diphenylmethyl 7β-phenylacetamido-3-[(1-tritylpyrazol-4-yl)methylthio]-3-cephem-4-carboxylate (6.8 g) was added to the above mixture at −10° C. and the reaction mixture was stirred under ice-cooling for 1 hour. Then, methanol (5.2 ml) was added to the reaction mixture at −20° C. and the resulting solution was stirred under ice-cooling for 1 hour. Water (40 ml) was added to the above mixture under ice-cooling, and stirred for 30 minutes at the same temperature. The aqueous layer was separated and the dichloromethane layer was reextracted with 1 mol hydrochloric acid (30 ml). The aqueous layer and 1 mol hydrochloric acid layer were combined ethyl acetate (50 ml) was added to the aqueous layer and then the mixture was adjusted to pH 3.5 with 30% aqueous sodium hydroxide under stirring. The organic layer was separated, washed with brine (20 ml) and dried over magnesium sulfate. The solvent was distilled off and the residue was pulverized with IPE (50 ml), collected by filtration, washed with IPE (20 ml) and dried over phosphorus pentoxide to give powder of diphenylmethyl 7β-amino-3-[(pyrazol-4-yl)methylthio]-3-cephem-4-carboxylate (2.1 g).

The physical data showed that the object compound is the same with the object compound of the Preparation 22.

PREPARATION 24

Diphenylmethyl 7β-amino-3-[(pyrazol-4-yl)methylthio]-3-cephem-4-carboxylate was obtained from 7β-formamido-3-[(pyrazol-4-yl)-methylthio]-3-cephem-4-carboxylate according to a similar manner to that of Preparation 23.

The physical data showed that the object compound is the same with the object compound of the Preparation 22.

PREPARATION 25

Diphenylmethyl 7β-formamido-3-[(pyrazol-4-yl)methylthio]-3-cephem-4-carboxylate (2.96 g) was dissolved in methanol (30 ml) and concentrated hydrochloric acid (2.2 ml) was added thereto at the room temperature. Stirring was continued for 3 hours, then solvent was evaporated. The residue was diluted with a mixture of water. The ethyl acetate and aqueous layer was adjusted to pH 6.5 with 30% aqueous potassium carbonate. The organic layer was separated, washed with water and brine, and dried over magnesium sulfate. Solvent was evaporated to afford diphenylmethyl 7β-amino-3-[(pyrazol-4-yl)methylthio]-3-cephem-4-carboxylate (1.50 g).

The physical data showed that the object compound is the same with the object compound of the Preparation 22.

PREPARATION 26

To a solution of diphenylmethyl 7β-formamido-3-[(1,2,3-thiadiazol-5-yl)thio]-3-cephem-4-carboxylate (3.99 g) in a mixture of methanol (20 ml) and THF (10 ml) was added concentrated hydrochloric acid (2.75 ml) at the room temperature. After stirring at the same temperature for 4 hours, the mixture was poured into a mixture of ice water and ethyl acetate. The mixture was adjusted to pH 4 with aqueous sodium bicarbonate solution. The organic layer was separated washed with water and brine, dried over magnesium sulfate, and evaporated to give diphenylmethyl 7β-amino-3-[(1,2,3-thiadiazol-5-yl)thio]-3-cephem-4-carboxylate (3.24 g).

IR (KBr): 1770.3, 1733.7, 1618.0 cm$^{-1}$; NMR (DMSO-d$_6$, δ): 3.49 and 3.83 (2H, ABq, J=17.8 Hz), 4.94 (1H, d, J=5.3 Hz), 5.13 (1H, d, J=5.3 Hz), 6.95 (1H, s), 7.25–7.39 (10H, m), 8.82 (1H, s).

PREPARATION 27

Diphenylmethyl 7β-amino-3-[(pyrazol-4-yl)methylthio]-3-cephem-4-carboxylate (810 mg) was dissolved in formic acid (3.2 ml) below 5° C. and herein concentrated hydrochloric acid (0.71 ml) was added thereto at the same temperature. After the reaction mixture was stirred at the room temperature for an hour, it was poured into a mixture of ethyl acetate (50 ml) and acetone (25 ml), resulting precipitate was collected by filtration, and dried under reduced pressure. The precipitate was suspended in a mixture of water (6.0 ml) and acetone (2.5 ml). After the suspension was dissolved at pH 7.0 with saturated sodium bicarbonate solution, and adjusted to pH 4.5 with 1N-hydrochloric acid. The mixture was stirred at the room temperature for 30 minutes, and then resulting precipitate was collected, washed with acetone (5.0 ml), and dried under reduced pressure to give 7β-amino-3-[(pyrazol-4-yl)methylthio]-3-cephem-4-carboxylic acid (0.36 g) was obtained.

IR (KBr): 1809, 1622, 1541 cm–1; NMR (DMSO-$d_6$, δ): 3.69, 3.81 (2H, ABq, J=14.0 Hz), 3.99 (2H, s), 4.72 (1H, d, J=4.9 Hz), 4.95 (1H, d, J=4.9 Hz), 7.54 (2H, s).

PREPARATION 28

Under nitrogen atmosphere, 28.0 ml of bis(trimethylsilyl)acetamide was added to a solution of 8.7 g of diphenylmethyl 7β-amino-3-methanesulfonyloxy-3-cephem-4-carboxylate in N,N-dimethylacetamide (100 ml) at 0° C. Stirring was continued for 30 minutes, (5-amino-1,2,4-thiadiazol-3-yl)-2-(Z)-(cyclopenten-3-yl)oxyiminoacetylchloride hydrochloride (7.0 g) was added portionwise at the same temperature. Stirring was continued another 1 hour, the mixture was poured into a mixture of water and ethyl acetate. The organic layer was separated, washed with water, brine and dried over magnesium sulfate. After evaporation of the solvent, the residue was purified on silica gel to afford diphenylmethyl 7β-[2-(5-amino-1,2,4-thiadiazol-3-yl)-2-[(Z)[(cyclopenten-3-yl)oxyimino]acetamido]-3-methanesulfonyloxy-3-cephem-4-carboxylate (10.4 g).

IR (KBr): 3342.0, 1793.5, 1733.7, 1683.6, 1621.8, 1525.4 cm$^{-1}$; NMR (DMSO-$d_6$, δ): 1.80–2.40 (4H, m), 3.18 (1H, s), 3.71, 4.00 (2H, ABq, J=18.2 Hz), 5.30–5.33 (2H, m), 5.85–5.98 (2H, m), 6.11–6.14 (1H, m), 6.91 (1H, s), 7.21–7.57 (10H, m), 8.14 (2H, s), 9.63 (1H, d, J=8.52 Hz).

PREPARATION 29

Under nitrogen atmosphere, sodium cyanide (540 mg) was added to a solution of 4-chloromethyl-1-tritylpyrazole (3.58 g) in dimethylsulfoxide (30 ml) at 50° C. After stirring for 1 hour, the mixture was poured into water. The organic layer was separated, washed with water and brine, and dried over magnesium sulfate. The solvent was evaporated, to afford 4-cyanomethyl-1-tritylpyrazole (3.41 g).

NMR (CDCl$_3$, δ): 3.55 (2H, s), 7.08–7.43 (16H, m), 7.61 (1H, s).

PREPARATION 30

20% Aqueous sodium hydroxide (15 ml) was added to a solution of 4-cyanomethyl-1-tritylpyrazole (1.74 g) in ethanol (5 ml) and the mixture was refluxed 8 hours. Then the mixture was diluted with water, and washed with ethyl acetate. The aqueous layer was adjusted to pH 1.0 with 6N hydrochloric acid, extracted with ethyl acetate. The organic layer was separated, washed with brine, and dried over magnesium sulfate. The solvent was evaporated to afford 2-[1-(tritylpyrazol-4-yl)]acetic acid (1.50 g).

NMR (DMSO-$d_6$, δ): 3.42 (2H, s), 7.00–7.38 (16H, m), 7.53 (1H, s).

PREPARATION 31

Under nitrogen atmosphere, 4-methoxycarbonylpyrazole (12.6 g) was added portionwise to a suspension of lithium aluminum hydride (7.59 g) in THF (150 ml) with ice cooling. After stirring for 8 hours at room temperature, the reaction mixture was quenched with 8 ml of water, 8 ml of 15% aqueous sodium hydroxide and 24 ml of water successively. Insoluble material was filtrated off, and the filtrate was concentrated in vacuo to afford 4-hydroxymethylpyrazole (6.1 g).

NMR (DMSO-$d_6$, δ): 4.37 (2H, s), 7.49 (2H, s).

PREPARATION 32

The following compounds were obtained according to a similar manner to that of Preparation 31.
(1) 1-(Trityl)-3(or 5)-(hydroxymethyl)pyrazole-(14.2 g) was obtained from ethyl [1-(trityl)pyrazol-3(or 5)-yl]carboxylate (19.1 g).

NMR (CDCl$_3$, δ): 4.67 (2H, d, J=5.42 Hz), 6.21 (1H, d, J=2.46 Hz), 7.11–7.31 (16H, m).

(2) 1-Trityl-4-(2-hydroxyethyl)pyrazole (6.84 g) was obtained from 2-[1-(trityl)pyrazol-4-yl]acetic acid (7.36 g).

NMR (CDCl$_3$, δ): 2.67 (2H, t, J=6.52 Hz), 3.65–3.75 (2H, m), 7.09–7.35 (16H, m), 7.53 (1H, s).

PREPARATION 33

The following compounds were obtained according to a similar manner to that of Preparation 7.
(1) Ethyl [1-(trityl)pyrazol-3(or 5)-yl]carboxylate NMR (CDCl$_3$, δ): 1.33 (3H, t, J=7.2 Hz), 4.34 (2H, q, J=7.14 Hz), 6.76 (1H, d, J=2.50 Hz), 7.10–7.40 (16H, m).

PREPARATION 34

The following compounds were obtained according to a similar manner to that of Preparation 10.
(1) 1-Trityl-3(or 5)-(methanesulfonyloxymethyl)pyrazole NMR (CDCl$_3$, δ): 2.75 (3H, s), 5.27 (2H, s), 6.35 (1H, d, J=2.48 Hz), 7.08–7.40 (15H, m), 7.37 (1H, d, J=2.46 Hz).
(2) 1-Trityl-4-(2-methanesulfonyloxyethyl)-pyrazole NMR (CDCl$_3$, δ): 2.89 (3H, s), 2.89 (2H, t, J=8.00 Hz), 4.28 (2H, t, J=6.98 Hz), 7.08–7.17 (5H, m), 7.24–7.34 (11H, m), 7.54 (1H, s).

PREPARATION 35

The following compounds were obtained according to a similar manner to that of Preparation 12.
(1) 1-Trityl-3(or 5)-(benzoylthiomethyl)pyrazole NMR (DMSO-$d_6$, δ): 4.29 (2H, s), 6.27 (1H, d, J=2.44 Hz), 7.00–7.95 (21H, m).
(2) 1-Trityl-4-(2-benzoylthioethyl)pyrazole NMR (DMSO-$d_6$, δ): 2.75 (2H, t, J=7.14 Hz), 3.23 (2H, t, J=6.98 Hz), 6.98–7.03 (6H, m), 7.23–7.33 (10H, m), 7.51–7.73 (4H, m), 7.85–7.89 (2H, m).
(3) 1-Trityl-4-(benzoylthiomethyl)pyrazole NMR (DMSO-$d_6$, δ): 4.15 (2H, s), 7.05–7.65 (20H, m), 7.90–8.00 (2H, m).

PREPARATION 36

Under nitrogen atmosphere, 28% sodium methoxide (3.85 g) was added dropwise to a solution of 2.29 g of 3.5- dimethyl-1,2,4-thiadiazole in ethanol (15 ml) at room temperature. After the mixture was stirred for 30 minutes at 60° C., diethyl oxalate (2.92 g) in ethanol (15 ml) was added to the mixture. After stirring for 2.5 hours, the solvent was evaporated, 5% hydrochloric acid was added to the residue. The resulting precipitate was collected by filtration, and dried under reduced pressure to afford ethyl 3-(3-methyl-1,2,4-thiadiazol-5-yl)-2-oxobutylate (3.2 g).

NMR (DMSO-$d_6$, $\delta$): 1.27 (3H, t, J=7.08 Hz), 2.44 (3H, s), 4.23 (2H, q, J=7.10 Hz), 6.72 (1H, s).

PREPARATION 37

10% Aqueous sodium hydrochloride (105.1 g) was added dropwise to a solution of ethyl 3-(3-methyl-1,2,4-thiadiazol-5-yl)-2-oxobutylate (24.2 g) and sodium bicarbonate (8.97 g) in water (250 ml) at 0° C. Stirring was continued for 20 minutes. A cooled mixture of 1.69 g of sodium hydroxide and 12 ml of water and 187 ml of methylene chloride was added to the solution under 5° C. The mixture was stirred for 2 hours at 0° C., then insoluble material was separated by filtration. The filtrate was extracted with methylene chloride, washed with brine, and dried over magnesium sulfate. After evaporation of the solvent, the residue was purified on silica gel (eluent: methylene chloride-n-hexane) to afford 5-chloromethyl-3-methyl-1,2,4-thiadiazole (8.3 g).

NMR (CDCl$_3$, $\delta$): 2.67 (3H, s), 4.89 (2H, s).

PREPARATION 38

Under nitrogen atmosphere, 1.7 ml of thionyl chloride was added to a suspension of 1.0 g of 4-hydroxymethylpyrazole in chloroform (25 ml) at room temperature. Stirring was continued for 30 minutes and the solvent was evaporated. The residue was washed with ether and dried under vacuo to afford 4-chloromethylpyrazole hydrochloride (1.29 g).

NMR (DMSO-$d_6$, $\delta$): 4.74 (2H, s), 7.96 (2H, s).

PREPARATION 39

Under nitrogen atomosphere, thiobenzoic acid (2.52 ml) was added dropwise to a solution of potassium tert-butoxide (2.30 g) in DMF (15 ml) under ice cooling. After stirring for 10 minutes, 2-chloromethyl-5-methyl-1,3,4-thiadiazole in DMF (15 ml) was added to the mixture. The whole mixture was and stirred for 45 minutes. The mixture was poured into a mixture of water and ethyl acetate, and the pH was adjusted to 8.5 with 30% aqueous sodium hydroxide. Organic layer was separated, was washed with water and brine, and dried over magnesium sulfate. After evaporation of the solvent, the residue was purified on silica gel (eluent: n-hexane-ethyllactate) to afford 2-methyl-5-benzoylthiomethyl-1,3,4-thiadiazole.

NMR (DMSO-$d_6$, $\delta$): 2.67 (3H, s), 4.74 (2H, s), 7.50–7.62 (2H, m), 7.69–7.78 (1H, m), 7.92–7.97 (2H, m).

PREPARATION 40

The following compounds were obtained according to a similar manner to that of Preparation 39.
(1) 1-Trityl-4-benzoylthioimidazole
NMR (DMSO-$d_6$, $\delta$): 4.20 (2H, s), 6.89 (1H, s), 7.04–7.72 (19H, m), 7.87–7.91 (2H, m).
(2) 3-Methyl-5-benzoylthiomethyl-1,2,4-thiadiazole
NMR (DMSO-$d_6$, $\delta$): 2.56 (3H, s), 4.79 (2H, s), 7.55–7.80 (3H, m), 7.94–8.00 (2H, m).
(3) 2-Methyl-5-benzoylthiomethyl-1,3,4-oxadiazole
IR (KBr): 1666.2, 1585.2, 1565.9 cm$^{-1}$;
NMR (DMSO-$d_6$, $\delta$): 2.48 (3H, s), 4.59 (2H, s), 7.55–7.79 (3H, m), 7.94–8.00 (2H, m).

PREPARATION 41

Under nitrogen atmosphere, 1-methyl-5-hydroxymethylimidazole (2.52 g), diethylazodicarboxylate (4.26 ml) was added successively to a solution of triphenylphosphine (7.07 g) in THFe (50 ml) with ice cooling, while the reaction temperature was kept below 15 degree. After stirring for 1 hour at 0° C., 3.9 ml of thiobenzoic acid was added slowly. The mixture was poured into a mixture of ethyl acetate and aqueous sodium hydrogen carbonate. The aqueous layer was separated, the organic layer was washed with water and brine, and dried over magnesium sulfate. After evaporation of the solvent, the residue was purified on silica gel (eluent: dichloromethane-acetone) to afford 1-methyl-5-(benzoylthiomethyl)imidazole (993 mg).

IR (CHCl$_3$): 1741.4, 1662.3, 1602.6 cm$^{-1}$; NMR (DMSO-$d_6$, $\delta$): 3.62 (3H, s), 4.40 (2H, s), 6.91 (1H, s), 7.52–7.74 (4H, m), 7.73–7.94 (2H, m).

PREPARATION 42

The following compounds were obtained according to a similar manner to that of Preparation 7.
(1) 3-Hydroxymethyl-1-trityl-1,2,4-triazole
NMR (DMSO-$d_6$, $\delta$): 4.44 (2H, d, J=6 Hz), 5.32 (1H, t, J=6 Hz), 7.0–7.1 (6H, m), 7.3–7.4 (9H, m), 8.04 (1H, s).

PREPARATION 43

The following compounds were obtained according to a similar manner to that of Preparation 10.
(1) 3-Methanesulfonyloxymethyl-1-triphenylmethyl-1,2,4-triazole
NMR (DMSO-$d_6$, $\delta$): 3.16 (3H, s), 5.29 (2H, s), 7.0–7.1 (6H, m), 7.3 (9H, m), 8.27 (1H, s).

PREPARATION 44

The following compounds were obtained according to a similar manner to that of Preparation 12.
(1) 5-Benzoylthiomethyl-1-(triphenylmethyl)-1,2,4-triazol
IR (KBr): 1668 cm$^{-1}$; NMR (DMSO-$d_6$, $\delta$): 4.39 (2H, s), 7.0–7.1 (6H, m), 7.3–7.4 (9H, m), 7.5–7.8 (3H, m), 7.9–8.0 (2H, m), 8.06 (1H, s).

EXAMPLE 1

Diphenylmethyl 7$\beta$-amino-3-[(4-pyridyl)methylthio]-3-cephem-4-carboxylate (2.15 g, 4.39 m mol) was dissolved in dichloromethane (50 ml) by addition of bis(trimethylsilyl)acetamide (1.79 g, 8.78 m mol). To a resulting solution was added 2-(2-aminothiazol-4-yl)-2-(Z)-(acetoxyimino)acetyl chloride hydrochloride (1.50 g, 5.27 m mol) at 5° C. and the mixture was stirred at 5° C. for 1.5 hours and at room temperature for 16 hours. The mixture was poured into a mixture of water and methanol and adjusted to pH 7 by addition of 1N NaOH aq. The organic layer was separated, washed with brine, dried over magnesium sulfate and evaporated in vacuo to give diphenylmethyl 7$\beta$-[2-(2-aminothiazol-4-yl)-2-(Z)-(acetoxyimino)acetamido]-3-[(4-pyridyl)methylthio]-3-cephem-4-carboxylate (2.37 g).

NMR (DMSO-$d_6$, $\delta$): 2.14 (3H, s), 3.75–3.85 (2H, m), 4.22 (2H, s), 5.27 (1H, d, J=5 Hz), 5.76 (1H, dd, J=8 and 5 Hz), 6.87 (1H, s), 7.2–7.6 (15H, m), 8.53 (2H, d, J=6.0 Hz), 9.90 (1H, d, J=8 Hz).

EXAMPLE 2

To a suspension of diphenylmethyl 7$\beta$-[2-(2-aminothiazol-4-yl)-2-(Z)-(acetoxyimino)acetamido]-3-[(4- pyridyl)methylthio]-3-cephem-4-carboxylate (2.37 g, 3.51 m mol) in a mixture of dichloromethane (12 ml) and anisole (2.4 ml) was added trifluoroacetic acid (4.8 ml) at 5° C. and the mixture was stirred at the same temperature for 2 hours. The mixture was poured into IPE (300 ml) and the precipitates were collected by filtration, washed with IPE and dried in vacuo. The powder was suspended in a mixture of water (150 ml) and methanol (7.5 ml), and ammonium chloride (563 mg, 10.5 m mol) was added thereto. The mixture was stirred at room temperature with keeping the pH to 8 by addition of saturated NaHCO$_3$ aqueous solution. The mixture was adjusted to pH ca. 6 by addition of 6N HCl and by evaporated in vacuo. The residue was adjusted to pH 3.5 by addition of 6N HCl and chromatographed on HP-20 (80 ml) and eluted with 5% aqueous IPA. The eluent was lyophilized and the crude product was purified by preparative HPLC to give 7β-[2-(2-aminothiazol-4-yl)-2-(Z)-(hydroxyimino) acetamido]-3-[(4-pyridyl)methylthio]-3-cephem-4-carboxylic acid (295 mg).

IR (Nujol): 1750, 1600, 1505 cm$^{-1}$; NMR (DMSO-d$_6$, δ): 3.70 (2H, s), 4.14 (2H, s), 5.13 (1H, d, J=4.7 Hz), 5.71 (1H, dd, J=8.2 and 4.7 Hz), 6.67 (1H, s), 7.13 (2H, br s), 7.35 (2H, dd, J=4.5 and 1.6 Hz), 8.51 (2H, dd, J=4.5 and 1.6 Hz), 9.46 (1H, d, J=8.2 Hz), 11.31 (1H, s).

EXAMPLE 3

To a solution of diphenylmethyl 7β-[2-(2-aminothiazol-4-yl)-2-(Z)-(acetoxyimino)acetamido]-3-[(3-pyridyl) methylthio]-3-cephem-4-carboxylate (3.32 g, 4.83 m mol) and anisole (3.3 ml) in dichloromethane (16.6 ml) was added trifluoroacetic acid (6.6 ml) at 5° C. The mixture was stirred at 5° C. for 1.5 hours. The reaction mixture was poured into IPE. The resulting precipitates were collected by filtration, washed with IPE, and dried in vacuo to give 7β-[2-(2-aminothiazol-4-yl)-2-(Z)-(acetoxyimino)acetamido]-3-[(3-pyridyl)methylthio]-3-cephem-4-carboxylic acid bis (trifluoroacetic acid) salt (3.88 g, 5.08 m mol).

IR (Nujol): 1740, 1620 cm$^{-1}$; NMR (DMSO-d$_6$, δ): 2.29 (3H, s), 3.83 (2H, s), 4.27 (2H, s), 5.21 (1H, d, J=5 Hz), 5.78 (1H, dd, J=5 and 8 Hz), 7.11 (1H, s), 7.8–7.9 (1H, m), 8.2–8.3 (1H, m), 8.7–8.8 (2H, m), 9.91 (1H, d, J=8 Hz).

EXAMPLE 4

A solution of 7β-[2-(2-aminothiazol-4-yl)-2-(Z)-(acetoxyimino)acetamido]-3-[(3-pyridyl)methylthio]-3-cephem-4-carboxylic acid bis(trifluoroacetic acid) salt (3.85 g, 5.05 m mol) and ammonium chloride (810 mg, 15.2 m mol) in a mixture of water (116 ml) and methanol (11.6 ml) was stirred at room temperature for 2.5 hours with keeping pH 8. The reaction mixture was adjusted to pH 6 by addition of 1N HCl. Methanol in the mixture was removed by evaporation in vacuo. The aqueous solution was adjusted to pH 5 and chromatographed on HP-20 (100 ml) and eluted with 5–10% aqueous isopropanol. The eluent was lyophilized. To the crude product was added water and acetonitrile. The precipitates were collected by filtration, washed with water and dried in vacuo to give 7β-[2-(2-aminothiazol-4-yl)-2-(Z)-(hydroxyimino)acetamido]-3-[(3-pyridyl)methyl-thio]-3-cephem-4-carboxylic acid (445 mg, 0.903 m mol).

IR (Nujol): 1770, 1650, 1580, 1520 cm$^{-1}$; NMR (DMSO-d$_6$, δ): 3.76 (2H, s), 4.13 and 4.19 (2H, ABq, J=13 Hz), 5.14 (1H, d, J=5 Hz), 5.17 (1H, dd, J=5 and 8 Hz), 6.68 (1H, s), 7.14 (2H, br s), 7.3–7.4 (1H, m), 7.7–7.8 (1H, m), 8.4–8.6 (2H, m), 9.48 (1H, d, J=8 Hz), 11.3 (1H, s).

EXAMPLE 5

The following compounds were obtained according to a similar manner to that of Example 1.

(1) Diphenylmethyl 7β-[2-(2-aminothiazol-4-yl)-2-(Z)-(acetoxyimino)acetamido]-3-[(3-pyridyl)methylthio]-3-cephem-4-carboxylate (3.35 g, 4.88 m mol).

IR (Nujol): 1760, 1670, 1600, 1520 cm–1; NMR(DMSO d-$_6$, δ): 2.19 (3H, s), 3.90 (2H, s), 4.21 (2H, s), 5.28 (1H, d, J=5 Hz), 5.85 (1H, dd, J=5 and 8 Hz), 6.85 (1H, s), 7.14 (1H, s), 7.2–7.4 (10H, m), 7.4–7.5 (1H, m), 7.6–7.8 (1H, m), 8.4–8.5 (2H, m), 9.93 (1H, d, J=8 Hz).

(2) Diphenylmethyl 7β-[2-(2-aminothiazol-4-yl)-2-(Z)-(acetoxyimino]acetamido)-3-[(1,2,3-thiadiazol-4-yl) methylthio]-3-cephem-4-carboxylate NMR (DMSO-d$_6$, δ): 2.19 (3H, s), 3.3–3.4 (2H, m), 4.71 (2H, s), 5.28 (1H, d, J=4.7 Hz), 5.86 (1H, dd, J=8.2 and 4.7 Hz), 6.83 (1H, s), 6.88 (1H, s), 7.2–7.5 (12H, m), 9.03 (1H, s), 9.94 (1H, d, J=8. 2 Hz).

(3) Diphenylmethyl 7β-[2-(2-aminothiazol-4-yl)-2-(Z)-(acetoxyimino)acetamido]-3-(3-pyridylthio)-3-cephem-4-carboxylate NMR (DMSO-d$_6$, δ): 2.20 (3H, s), 3.3–3.7 (2H, m), 5.29 (1H, d, J=4.8 Hz), 5.91 (1H, dd, J=8.2 and 4.8 Hz), 6.90 (1H, s), 7.07 (1H, s), 7.2–7.5 (13H, m), 7.7–7.85 (1H, m), 8.5–8.6 (2H, m), 9.93 (1H, d, J=8.2 Hz).

EXAMPLE 6

The following compounds were obtained according to a similar manner to that of Example 2.

(1) 7β-[2-(2-Aminothiazol-4-yl)-2-(Z)-(hydroxyimino) acetamido]-3-[(1,2,3-thiadiazol-4-yl)methylthio]-3-cephem-4-carboxylic acid IR (Nujol): 1750, 1630, 1520 cm$^{-1}$; NMR (DMSO-d$_6$, δ): 3.80 and 3.91 (2H, ABq, J=17.2 Hz), 4.63 (2H, s), 5.15 (1H, d, J=4.7 Hz), 5.72 (1H, dd, J=8.2 and 4.7 Hz), 6.68 (1H, s), 7.14 (2H, br s), 9.04 (1H, s), 9.48 (1H, d, J=8.2 Hz).

(2) 7β-[2-(2-Aminothiazol-4-yl)-2-(Z)-(hydroxyimino) acetamido]-3-(3-pyridylthio)-3-cephem-4-carboxylic acid IR (Nujol): 1750, 1600 cm$^{-1}$; NMR (DMSO-d$_6$, δ): 3.22 and 3.62 (2H, ABq, J=17.3 Hz), 5.22 (1H, d, J=4.9 Hz), 5.79 (1H, dd, J=8.2 and 4.9 Hz), 6.64 (1H, s), 7.12 (2H, br s), 7.35–7.45 (1H, m), 7.8–7.9 (1H, m), 8.5–8.6 (2H, m), 9.52 (1H, d, J=8.2 Hz), 11.32 (1H, s).

EXAMPLE 7

To a solution of diphenylmethyl 7β-[2-(2-tritylaminothiazol-4-yl)-2-(Z)-(trityloxyimino)acetamido]-3-methanesulfonyloxy-3-cephem-4-carboxylate (10.01 g, 8.98 m mol) in DMF (200 ml) was added 4-mercaptopyridine (2.00 g, 18.0 m mol) at −15° C., followed by dropwise addition of N,N-diisopropylethylamine (1.16 g, 8.98 m mol). The mixture was stirred at −15° C. for 4.5 hours and at 5° C. for 1 hour. The mixture was poured into a mixture of ice water (1.2 l) and 6N HCl (3 ml) and the precipitates were collected by filtration and washed with water. The powder was dissolved in THF, and ethyl acetate and water were added. The separated organic layer was washed with brine, dried over magnesium sulfate and evaporated in vacuo. The residue was purified by column chromatography on silica gel to give diphenylmethyl 7β-[2-(2-tritylaminothiazol-4-yl)-2-(Z)-(trityloxyimino)acetamido]-3-(4-pyridylthio)-3-cephem-4-carboxylate (1.37 g).

IR (Nujol): 1770, 1730, 1660, 1520 cm$^{-1}$; NMR (DMSO-d$_6$, δ): 3.3–3.5 (2H, m), 5.25 (1H, d, J=4.4 Hz), 5.75 (1H, dd, J=8.4 and 4.4 Hz), 6.91 (1H, s), 7.1–7.6 (33H, m), 8.43 (2H, d, J=6.2 Hz), 8.77 (1H, s), 9.86 (1H, d, J=8.4 Hz).

EXAMPLE 8

To a suspension of diphenylmethyl 7β-[2-(2-tritylaminothiazol-4-yl)-2-(Z)-(trityloxyimino)acetamido]-

3-(4-pyridylthio)-3-cephem-4-carboxylate (1.37 g, 1.21 m mol) in anisole (2.7 ml) was added trifluoroacetic acid (5.4 ml) at 5° C. and the resulting solution was stirred at room temperature for 4 hours. The mixture was poured into IPE (150 ml) and the precipitates were collected by filtration, washed with IPE and dried in vacuo. The powder was dissolved in water (100 ml) by addition of saturated NaHCO$_3$ aqueous solution. The solution was adjusted to pH 6 by addition of 1N HCl and chromatographed on HP-20 (50 ml) and eluted with 10% aqueous IPA. The eluent was lyophilized and the crude product was purified by preparative HPLC to give 7β-[2-(2-aminothiazol-4-yl)-2-(Z)-(hydroxyimino)acetamido]-3-(4-pyridylthio)-3-cephem-4-carboxylic acid (52 mg).

IR (Nujol): 1750, 1620, 1590, 1530 cm$^{-1}$; NMR (DMSO-d$_6$, δ): 3.32 and 3.86 (2H, ABq, J=17.6 Hz), 5.33 (1H, d, J=5.0 Hz), 5.89 (1H, dd, J=8.2 and 5.0 Hz), 6.65 (1H, s), 7.13 (2H, br s), 7.21 (2H, dd, J=4.6 and 1.6 Hz), 8.45 (2H, dd, J=4.6 and 1.6 Hz), 9.59 (1H, d, J=8.2 Hz), 11.33 (1H, s).

EXAMPLE 9

7-β-[2-(2-Aminothiazol-4-yl)-2-(Z)-(hydroxyimino) acetamide]-3-[(1,2,3-thiadiazol-4-yl)methylthio]-3-cephem-4-carboxylic acid(0.34 g) was obtained by reacting 7-β-amino-3-[(1,2,3-thiadiazol-4-yl)methylthio]-3-cephem-4-carboxylic acid hydrochloride (2.62 g) with 2-(2-aminothiazol-4-yl)-2-(Z)-(acetoxyimino)acetyl chloride hydrochloride (2.43 g) in a similar manner to that of Example 1 followed by hydrolyzing with ammonium chloride in a similar manner to that of Example 4. The physical data showed the object compound is the same with the Example 6(1).

EXAMPLE 10

To a solution of 2-(2-aminothiazol-4-yl)-2-(Z)-(trityloxyimino)acetic acid (3.70 g, 8.61 m mol) in N,N-dimethylacetamide (37 ml) was added potassium carbonate (1.19 g, 8.61 m mol) and methansulfonyl chloride (1.33 ml, 17.2 m mol) at 5° C. The mixture was stirred at 5° C. for 30 minutes. To a solution of 7β-amino-3-[(pyrazin-2-yl)methylthio]-3-cephem-4-carboxylic acid hydrochloride (3.42 g, 8.61 m mol) in DMF (34.2 ml) was added bis(trimethylsilyl)acetamide (14.9 ml, 60.3 m mol), and stirred at 5° C. for 20 minutes. To the solution was added the above-mentioned solution of the activated acid. The mixture was stirred at 5° C. for 1 hour. The reaction mixture was poured into 20% NaCl aq. (350 ml). The precipitates were collected by filtration, washed with water and dried in vacuo to give 7β-[2-(2-aminothiazol-4-yl)-2-(Z)-(trityloxyimino) acetamido]-3-[(pyrazin-2-yl)methylthio]-3-cephem-4-carboxylic acid (6.98 g, 9.49 m mol).

IR (KBr): 1778, 1668, 1625 cm$^{-1}$; NMR (DMSO-d$_6$, δ): 3.75 and 3.87 (2H, ABq, J=18 Hz), 4.25 (2H, s), 5.18 (1H, d, J=5 Hz), 5.80 (1H, dd, J=5 and 8 Hz), 6.65 (1H, s), 7.1–7.4 (17H, m), 8.4–8.6 (3H, m), 9.88 (1H, d, J=8 Hz).

EXAMPLE 11

The following compounds were obtained according to a similar manner to that of Example 7.
(1) Diphenylmethyl 7β-[2-(2-aminothiazol-4-yl)-2-(Z)-(trityloxyimino)acetamido]-3-[(pyrimidin-4-yl)methylthio]-3-cephem-4-carboxylate IR (KBr): 1786, 1684 cm$^{-1}$; NMR (DMSO-d$_6$, δ): 3.90 (2H, s), 4.31 (2H, s), 5.30 (1H, d, J=5 Hz), 5.94 (1H, dd, J=5 and 8 Hz), 6.68 (1H, s), 6.88 (1H, s), 7.2–7.6 (18H, m), 8.73 (1H, d, J=5 Hz), 9.09 (1H, s), 9.88 (1H, d, J=8 Hz).

(2) Diphenylmethyl 7β-[2-(2-aminothiazol-4-yl)-2-(Z)-(trityloxyimino)acetamido]-3-[(pyridazin-3-yl)methylthio]-3-cephem-4-carboxylate IR (KBr): 1784, 1728, 1684 cm$^{-1}$; NMR (DMSO-d$_6$, δ): 3.96 (2H, s), 4.51 (2H, s), 5.29 (1H, d, J=5 Hz), 5.95 (1H, dd, J=5 and 8 Hz), 6.68 (1H, s), 6.87 (1H, s), 7.1–7.7 (29H, m), 7.66 (2H, d, J=3 Hz), 9.13 (1H, t, J=3 Hz), 9.92 (1H, d, J=9 Hz).

(3) Diphenylmethyl 7β-[2-(2-aminothiazol-4-yl)-2-(Z)-(trityloxyimino)acetamido]-3-[2-(pyridin-4-yl)ethylthio]-3-cephem-4-carboxylate IR (KBr): 1784, 1682 cm$^{-1}$; NMR (DMSO-d$_6$, δ): 2.85 (2H, t, J=7 Hz), 3.20 (2H, t, J=7 Hz), 3.88 (2H, s), 5.33 (1H, d, J=5 Hz), 5.95 (1H, dd, J=5 and 8 Hz), 6.71 (1H, s), 6.89 (1H, s), 7.2–7.6 (19H, m), 8.45 (1H, d, J=6 Hz), 9.90 (1H, d, J=8 Hz).

EXAMPLE 12

Under nitrogen atmosphere, 1.35 ml of sodium methoxide (6.5 m mol) was added slowly to a solution of 1.50 g of 1-methyl-4-benzoylthiomethylpyrazole (6.5 m mol) in THF (6 ml) and DMF (18 ml) at 0° C. Stirring was continued for 1 hour. The mixture was cooled to −65° C. with dry ice/ethanol bath, and added to a solution of 4.36 g of diphenylmethyl 7β-[2-(2-aminothiazol-4-yl)-2-(Z)-(trityloxyimino)acetamido]-3-methanesulfonyloxy-3-cephem-4-carboxylate (5 m mol) in a mixture of THF (15 ml) and DMF (25 ml) at the same temperature. After stirring for 1 hour, the reaction was quenched with 10% hydrochloric acid, and the mixture was poured into water-ethyl acetate. The organic layer was separated washed with brine, dried over magnesium sulfate. After filtration, the filtrate was concentrated in vacuo, the residue was purified on silica gel (eluent: dichloromethane-acetone) to afford a diphenylmethyl 7β-[2-(2-aminothiazol-4-yl)-2-(Z)-(trityloxyimino) acetamido]-3-[(1-methylpyrazol-4-yl)methylthio]-3-cephem-4-carboxylate (2.15 g).

NMR (DMSO-d$_6$, δ): 3.71 (3H, s), 3.87 (2H, s), 4.05 (2H, d, J=4.3 Hz), 5.31 (1H, d, J=4.62 Hz), 5.93 (1H, dd, J=8.52 and 4.54 Hz), 6.70 (1H, s), 6.83 (1H, d, J=2.36 Hz), 6.86 (1H, s), 7.19–7.59 (26H, m), 9.88 (1H, d, J=8.52 Hz).

EXAMPLE 13

The following compounds were obtained according to a similar manner to that of Example 12.
(1) Diphenylmethyl 7β-[2-(2-aminothiazol-4-yl)-2-(Z)-(trityloxyimino)acetamido]-3-[(1,2,3-thiadiazol-5-yl)methylthio]-3-cephem-4-carboxylate
(2) Diphenylmethyl 7β-[2-(2-aminothiazol-4-yl)-2-(Z)-(trityloxyimino)acetamido]-3-[(1-tritylpyrazol-4-yl)methylthio]-3-cephem-4-carboxylate NMR (DMSO-d$_6$, δ): 3.81 (2H, s), 4.07 (2H, s), 5.25 (1H, d, J=4.6 Hz), 5.91 (1H, dd, J=8.4 and 4.6 Hz), 6.71 (1H, s), 6.86 (1H, s), 6.99–7.03 (6H, m), 7.20–7.57 (36H, m), 9.87 (1H, d, J=8.6 Hz).

(3) Diphenylmethyl 7β-[2-(2-aminothiazol-4-yl)-2-(Z)-(trityloxyimino)acetamido]-3-[(4-methyl-1,2,3-thiadiazol-5-yl)methylthio]-3-cephem-4-carboxylate NMR (DMSO-d$_6$, δ): 2.56 (3H, s), 3.76 and 3.91 (2H, ABq, J=17.1 Hz), 4.57 (2H, s), 5.32 (1H, d, J=4.72 Hz), 5.99 (1H, dd, J=8.5 and 4.7 Hz), 6.65 (1H, s), 6.89 (1H, s), 7.20–7.60 (25H, m), 9.92 (1H, d, J=8.5 Hz).

(4) Diphenylmethyl 7β-[2-(2-aminothiazol-4-yl)-2-(Z)-(trityloxyimino)acetamido]-3-[(1,2,5-thiadiazol-3-yl)methylthio]-3-cephem-4-carboxylate NMR (DMSO-d$_6$, δ): 4.19 and 4.42 (2H, ABq, J=14.4 Hz), 4.56 (2H, s), 5.31 (1H, d, J=4.7 Hz), 5.95 (1H, dd, J=8.5 and 4.7 Hz), 6.68 (1H, s), 6.88 (1H, s), 7.15–7.60 (25H, m), 8.74 (1H, s), 9.94 (1H, d, J=8.5 Hz).

EXAMPLE 14

A solution of 7β-[2-(2-aminothiazol-4-yl)-2-(Z)-(trityloxyimino)acetamido]-3-[(pyrazin-2-yl)methylthio]-3-cephem-4-carboxylic acid (1.5 g, 2.04 m mol) in 90% formic acid aqueous solution was stirred at room temperature for 2 hours. Insoluble material in the reaction mixture was filtered off. The filtrate was adjusted to pH 3 and washed with ethyl acetate. The aqueous solution was chromatographed on HP-20 and eluted with 5–14% isopropanol aqueous solution. The eluent was lyophilized to give crude product (275 mg). The crude product was purified with preparative HPLC to give 7β-[2-(2-aminothiazol-4-yl)-2-(Z)-(hydroxyimino) acetamido]-3-[(pyrazin-2-yl)methylthio]-3-cephem-4-carboxylic acid (131 mg, 0.265 m mol).

IR (KBr): 1768, 1668, 1653 cm$^{-1}$; NMR (DMSO-d$_6$, δ): 3.74 and 3.87 (2H, ABq, J=18 Hz), 4.27 (2H, s), 5.12 (1H, d, J=5 Hz), 5.71 (1H, dd, J=5 and 8 Hz), 6.68 (1H, s), 7.14 (2H, s), 8.5–8.7 (3H, m), 9.49 (1H, d, J=8 Hz), 11.3 (1H, s).

EXAMPLE 15

To a solution of diphenylmethyl 7β-[2-(2-aminothiazol-4-yl)-2-(Z)-(trityloxyimino)acetamido]-3-[(pyrimidin-4-yl) methylthio]-3-cephem-4-carboxylate (1.57 g, 1.74 m mol) in formic acid (6.28 ml) was added conc. HCl (0.435 ml, 5.22 m mol) at 5° C. The mixture was stirred at room temperature for 1 hour. The reaction mixture was poured into a mixture of ethyl acetate (43 ml) and acetone (22 ml). The precipitates were collected by filtration, and dried in vacuo. The crude product was desalted with HP-20. The eluent was concentrated to give precipitates. The precipitates were collected by filtration and dried in vacuo to give 7β-[2-(2-aminothiazol-4-yl)-2-(Z)-(hydroxyimino)acetamido]-3-[(pyrimidin-4-yl) methylthio]-3-cephem-4-carboxylic acid (128 mg, 0.259 m mol).

IR (KBr): 1767, 1664, 1635 cm$^{-1}$; NMR (DMSO-d$_6$, δ): 3.75 and 3.85 (2H, ABq, J=17 Hz), 4.21 (2H, s), 5.13 (1H, d, J=5 Hz), 5.71 (1H, dd, J=5 and 8 Hz), 6.67 (1H, s), 7.13 (2H, s), 7.52 (1H, d, J=5 Hz), 8.75 (1H, d, J=5 Hz), 9.10 (1H, s), 9.47 (1H, d, J=8 Hz), 11.3 (1H, s).

EXAMPLE 16

The following compounds were obtained according to a similar manner to that of Example 15.

(1) 7β-[2-(2-Aminothiazol-4-yl)-2-(Z)-(hydroxyimino) acetamido]-3-[(pyridazin-3-yl)methylthio]-3-cephem-4-carboxylic acid IR (KBr): 1767, 1660 cm$^{-1}$; NMR (DMSO-d$_6$, δ): 3.78 and 3.88 (2H, ABq, J=17 Hz), 4.41 (2H, s), 5.11 (1H, d, J=5 Hz), 5.71 (1H, dd, J=5 and 8 Hz), 6.68 (1H, s), 7.14 (2H, s), 7.4–7.5 (2H, m), 9.1–9.2 (1H, m), 9.48 (1H, d, J=8 Hz), 11.3 (1H, s).

(2) 7β-[2-(2-Aminothiazol-4-yl)-2-(Z)-(hydroxyimino) acetamido]-3-[2-(pyridin-4-yl)ethylthio]-3-cephem-4-carboxylic acid IR (KBr): 1767, 1668, 1639, 1618 cm$^{-1}$; NMR (DMSO-d$_6$, δ): 2.7–2.9 (2H, m), 3.13 (2H, t, J=7 Hz), 3.73 and 3.83 (2H, ABq, J=17 Hz), 5.18 (1H, d, J=5 Hz), 5.73 (1H, dd, J=5 and 8 Hz), 6.69 (1H, s), 7.15 (2H, s), 7.33 (2H, d, J=5 Hz), 8.51 (2H, d, J=5 Hz), 9.48 (1H, d, J=8 Hz), 11.3 (1H, s).

(3) 7β-[2-(2-Aminothiazol-4-yl)-2-(Z)-(hydroxyimino) acetamido]-3-[(1-methylpyrazol-4-yl)methylthio]-3-cephem-4-carboxylic acid IR (KBr): 3332.4, 1770.3, 1666.2, 1612.2, 1535.1 cm$^{-1}$; NMR (DMSO-d$_6$, δ): 3.45 and 3.63 (2H, ABq, J=16.92 Hz), 3.87 (3H, s), 5.03 (1H, d, J=4.70 Hz), 5.62 (2H, dd, J=8.16 and 4.66 Hz), 6.66 (1H, s), 7.12 (1H, s), 7.32 (1H, s), 7.60 (1H, s), 9.42 (1H, d, J=8.16 Hz).

EXAMPLE 17

Under N$_2$ atmosphere, a solution of aluminum chloride (1.88 g, 14.05 m mol) in anisole (4.5 ml) was added slowly to a solution of diphenylmethyl 7β-[2-(2-aminothiazol-4-yl)-2-(Z)-(trityloxyimino)acetamido]-3-[(4-methyl-1,2,3-thiadiazol-5-yl)methylthio]-3-cephem-4-carboxylate (2.60 g, 2.81 m mol) in anisole (4.5 ml) and nitromethane (18 ml) at −30∼20° C. After the mixture was stirred for 1 hour at the same temperature, the reaction was quenched with 1N hydrochloric acid (18 ml), and poured into water/ethyl acetate. The aqueous layer was separated, and the organic layer was reextracted with water. The combined aqueous layer was concentrated in vacuo, chromatographed on a HP-20 column (eluent: water-methanol). After concentration, the resulting precipitate was collected by filtration, and dried in vacuo to afford 7β-[2-(2-aminothiazol-4-yl)-2-(Z)-(hydroxyimino)acetamido]-3-[(4-methyl-1,2,3-thiadiazol-5-yl)methylthio]-3-cephem-4-carboxylic acid (150.8 mg).

IR (KBr): 1768, 1646, 1556 cm$^{-1}$; NMR (DMSO-d$_6$, δ): 2.58 (3H, s), 3.71 (2H, br, s), 4.50 (2H, s), 5.15 (1H, d, J=4.8 Hz), 5.75 (1H, dd, J=8.14 and 4.74 Hz), 6.66 (1H, s), 7.13 (2H, s), 9.49 (1H, d, J=8.26 Hz), 11.31 (1H, s).

EXAMPLE 18

The following compounds were obtained according to a similar manner to that of Example 17.

(1) 7β-[2-(2-Aminothiazol-4-yl)-2-(Z)-(hydroxyimino) acetamido]-3-[(1,2,5-thiadiazol-3-yl)methylthio]-3-cephem-4-carboxylic acid IR (KBr): 3350, 1766, 1662, 1641 cm$^{-1}$; NMR (DMSO-d$_6$, δ): 3.73 (2H, d, J=19.2 Hz), 4.46 (2H, s), 5.13 (1H, d, J=4.7 Hz), 5.71 (1H, dd, J=8.2 and 3.5 Hz), 6.66 (1H, s), 7.13 (1H, s), 8.78 (1H, s), 9.48 (1H, d, J=8.2 Hz), 11.31 (1H, s).

(2) 7β-[2-(2-Aminothiazol-4-yl)-2-(Z)-(hydroxyimino) acetamido]-3-[1,2,3-thiadiazol-5-yl)methylthio]-3-cephem-4-carboxylic acid NMR (DMSO-d$_6$, δ): 3.73 (2H, s), 4.61 (2H, s), 5.16 (1H, d, J=4.78 Hz), 5.74 (1H, dd, J=8.16 and 4.72 Hz), 6.66 (1H, s), 7.14 (2H, s), 8.84 (1H, s), 9.50 (1H, d, J=8.24 Hz), 11.32 (1H, s).

EXAMPLE 19

The following compounds were obtained according to a similar manner to that of Example 12.

(1) Diphenylmethyl 7β-3-[2-(2-aminothiazol-4-yl)-2-(Z)-(trityloxyimino)acetamido]-3-[(1-tritylpyrazol-3(or 5)-yl) methylthio]-3-cephem-4-carboxylate (6.0 g).

NMR (DMSO-d$_6$, δ): 3.87 (2H, s), 4.15 (2H, d, J=6.1 Hz), 4.98 (1H, d, J=4.7 Hz), 5.90 (1H, dd, J=8.5 Hz, 4.7 Hz), 6.22 (1H, d, J=2.4 Hz), 6.68 (1H, s), 6.89–7.60 (27H, m), 9.89 (1H, d, J=8.5 Hz).

(2) Diphenylmethyl 7β-[2-(2-aminothiazol-4-yl)-2-(Z)-(trityloxyimino)acetamido]-3-[(3-tritylimidazol-4-yl) methylthio]-3-cephem-4-carboxylate NMR (DMSO-d$_6$, δ): 3.68 (2H, s), 4.08 (2H, s), 5.24 (1H, d, J=4.6 Hz), 5.90 (1H, dd, J=8.2 Hz, 4.6 Hz), 6.72 (1H, s), 6.81–7.58 (33H, m), 9.88 (1H, d, J=8.2 Hz).

(3) Diphenylmethyl 7β-[2-(2-aminothiazol-4-yl)-2-(Z)-(trityloxyimino)acetamido]-3-[(2-methyl-1,3,4-thiadiazol-5-yl)methylthio]-3-cephem-4-carboxylate NMR (DMSO-d$_6$, δ): 2.62 (3H, s), 3.85, 3.92 (2H, ABq, J=15.1 Hz), 4.67 (2H, s), 5.29 (1H, d, J=4.74 Hz), 5.96 (1H, dd, J=8.64 Hz, 4.80 Hz), 6.67 (1H, s), 6.89 (1H, s), 7.26–7.58 (25H, m), 9.91 (1H, d, J=8.54 Hz).

(4) Diphenylmethyl 7β-[2-(2-aminothiazol-4-yl)-2-(Z)-(trityloxyimino)acetamido]-3-[(3-methyl-1,2,4-thiadiazol-5-yl)methylthio]-3-cephem-4-carboxylate IR (KBr): 1785.8, 1675.8, 1618.0, 1537.0 cm$^{-1}$; NMR (DMSO-d$_6$, δ): 2.53 (3H, s), 3.82, 3.90 (2H, ABq, J=16.88 Hz), 4.72 (2H, s), 5.31 (1H, d, J=4.72 Hz), 5.97 (1H, dd, J=8.54, 4.70 Hz), 6.66 (1H, s), 6.91 (1H, s), 7.20–7.60 (28H, m), 9.89 (1H, d, J=8.58 Hz).

(5) Diphenylmethyl 7β-[2-(2-aminothiazol-4-yl)-2-(Z)-(trityloxyimino)acetamido]-3-[2-(1-tritylpyrazol-4-yl)ethylthio]-3-cephem-4-carboxylate IR (KBr): 3442.3, 1785.8, 1687.4, 1616.1 cm$^{-1}$; NMR (DMSO-d$_6$, δ): 2.56–2.65 (2H, m), 3.00–3.15 (2H, m), 3.82 (2H, s), 5.28 (1H, d, J=4.64 Hz), 5.92 (1H, dd, J=8.54 Hz, 4.54 Hz), 6.70 (1H, s), 6.87 (1H, s), 6.99–7.58 (43H, m), 9.87 (1H, d, J=8.54 Hz).

(6) Diphenylmethyl 7β-[2-(2-aminothiazol-4-yl)-2-(Z)-(trityloxyimino)acetamido]-3-[(1-methylimidazol-5-yl)methylthio]-3-cephem-4-carboxylate IR (KBr): 3440.4, 3060.5, 1785.8, 1681.6, 1616.1, 1573.1 cm−1;

NMR (DMSO-d$_6$, δ): 3.51 (3H, s), 3.89 (2H, s), 4.23 (2H, s), 5.31 (1H, d, J=4.72 Hz), 5.96 (1H, dd, J=8.52 Hz, 4.70 Hz), 6.68 (1H, s), 6.79 (1H, s), 6.89 (1H, s), 7.25–7.60 (28H, m), 9.91 (1H, d, J=8.54 Hz).

(7) Diphenylmethyl 7β-[2-(2-aminothiazol-4-yl)-2-(Z)-(trityloxyimino)acetamido]-3-[(2-methyl-1,3,4-oxadiazol-5-yl)methylthio]-3-cephem-4-carboxylate (8) Diphenylmethyl 7β-[2-(5-amino-1,2,4-thiadiazol-3-yl)-2-(Z)-(cyclopenten-3-yloxy)iminoacetamido]-3-[(1-tritylpyrazol-4-yl)methylthio]-3-cephem-4-carboxylate IR (KBr): 1781.9, 1683.9, 1618.0, 1519.6 cm$^{-1}$; NMR (DMSO-d$_6$, δ): 3.39 (3H, s), 3.79 (2H, s), 4.03 (2H, s), 5.12 (1H, d, J=4.76 Hz), 5.30–5.41 (1H, m), 5.80–5.93 (2H, m), 6.06–6.12 (1H, m), 6.83 (1H, s), 7.00–7.60 (12H, m), 8.15 (2H, s), 9.57 (1H, d, J=8.82 Hz).

(9) Diphenylmethyl 7β-[2-(2-aminothiazol-4-yl)-2-(Z)-(methoxyimino)acetamido]-3-[1,2,3-thiadiazol-5-yl)methylthio]-3-cephem-4-carboxylate (1.04 g)

NMR (DMSO-d$_6$, δ): 3.84 (5H, s), 4.66 (2H, s), 5.25 (1H, d, J=4.76 Hz), 5.82 (1H, dd, J=8.28 Hz, 4.60 Hz), 6.69 (1H, s), 6.86 (1H, s), 7.20–7.55 (25H, m), 8.85 (1H, s), 9.65 (1H, d, J=8.40 Hz).

(10) Diphenylmethyl 7β-[2-(2-aminothiazol-4-yl)-2-(Z)-(methoxyimino)acetamido]-3-[(2-methyl-1,3,4-thiadiazol-5-yl)methylthio]-3-cephem-4-carboxylate NMR (DMSO-d$_6$, δ): 2.65 (3H, s), 3.85 (3H, s), 3.87 (2H, s), 4.65 (2H, s), 5.21 (1H, d, J=4.66 Hz), 5.82 (1H, dd, J=8.38 Hz, 4.62 Hz), 6.78 (1H, s), 6.86 (1H, s), 7.24–7.52 (12H, m), 9.66 (1H, d, J=8.40 Hz).

(11) Diphenylmethyl 7β-[2-(2-aminothiazol-4-yl)-2-(Z)-(methoxyimino)acetamido]-3-[(3-methyl-1,2,4-thiadiazol-5-yl)methylthio]-3-cephem-4-carboxylate IR (KBr): 3322.7, 1791.5, 1677.8, 1614.1, 1533.1 cm$^{-1}$; NMR (DMSO-d$_6$, δ): 2.53 (3H, s), 3.84 (5H, s), 4.69, 4.71 (2H, ABq, J=16.12 Hz), 5.22 (1H, d, J=4.64 Hz), 5.82 (1H, dd, J=8.32 Hz, 4.66 Hz), 6.78 (1H, s), 6.88 (1H, s), 7.20–7.55 (13H, m), 9.64 (1H, d, J=8.38 Hz).

(12) Diphenylmethyl 7β-[2-(2-aminothiazol-4-yl)-2-(Z)-(methoxyimino)acetamido]-3-[(1-tritylpyrazol-4-yl)methylthio]-3-cephem-4-carboxylate NMR (DMSO-d$_6$, δ): 3.79 (2H, s), 3.85 (3H, s), 4.05 (2H, s), 5.16 (1H, d, J=4.56 Hz), 5.77 (1H, dd, J=8.26, 4.48 Hz), 6.75 (1H, s), 6.80 (1H, s), 6.90–7.60 (27H, m), 9.66 (1H, d, J=8.20 Hz).

EXAMPLE 20

Under nitrogen atmosphere, to a suspension of diphenylmethyl 7β-amino-3-[(pyrazol-4-yl)methylthio]-3-cephem-4-carboxylate (30.2 g) in THF (800 ml) was added herein 1,3-bis(trimethylsilyl)urea (25.8 g) was added at the room temperature. The reaction mixture was warmed at 35° C. and dissolved, and then it was cooled below 0° C. A suspension of 2-(2-aminothiazol-4-yl)-2-(Z)-(acetoxyimino)acetylchloride monohydrochiloride salt (17.93 g) in acetonitrile (200 ml) was dropped into the above reaction mixture below 0° C. After stirring at the same temperature for 10 minutes, it was poured into a mixture of ethyl acetate (1.2 l) and ice-water (1.5 l). The aqueous layer was adjusted at pH 6.5 with saturated sodium bicarbonate solution. The organic layer was separated, washed with brine (1.0 l), and dried over magnesium sulfate, and then evaporated until the volume amounted to 500 ml. The solution was poured into IPE (1.5 l). The resulting precipitate was filtered, dried under reduced pressure to give diphenylmethyl 7β-[2-(2-aminothiazol-4-yl)-2-(Z)-(acetoxyimino)acetamido]-3-[(pyrazol-4-yl)methylthio]-3-cephem-4-carboxylate (41.3 g) as powder.

IR (KBr): 1772, 1684, 1616, 1533, 1375, 1219 cm$^{-1}$; NMR (DMSO-d$_6$, δ): 2.17 (3H, s), 3.83–4.07 (4H, m), 5.26 (1H, d, J=4.6 Hz), 5.82 (1H, dd, J=4.6 Hz, 8.2 Hz), 6.83 (1H, s), 7.13 (1H, s), 7.23–7.52 (14H, m), 9.90 (1H, d, J=8.2 Hz), 12.75 (1H, s); FAB-Mass: 690 (M$^+$+1).

EXAMPLE 21

The following compounds were obtained according to a similar manner to that of Example 15.

(1) 7β-[2-(2-Aminothiazol-4-yl)-2-(Z)-(hydroxyimino)acetamido]-3-[(imidazol-4-yl)methylthio]-3-cephem-4-carboxylic acid IR (KBr): 3332.4, 1770.3, 1666.2, 1612.2, 1535.1 cm$^{-1}$; NMR (DMSO-d$_6$, δ): 3.45, 3.63 (2H, ABq, J=16.92 Hz), 3.87 (3H, s), 5.03 (1H, d, J=4.7 Hz), 5.62 (2H, dd, J=8.16, 4.66 Hz), 6.66 (1H, s), 7.12 (1H, s), 7.32 (1H, s), 7.60 (1H, s), 9.42 (1H, d, J=8.16 Hz).

(2) 7β-[2-(2-Aminothiazol-4-yl)-2-(Z)-(hydroxyimino)acetamido]-3-[(1-methylimidazol-5-yl)methylthio]-3-cephem-4-carboxylic acid IR (KBr): 3334.3, 1766.5, 1666.2, 1608.3, 1535.1 cm$^{-1}$; NMR (DMSO-d$_6$, δ): 3.62 (3H, s), 3.67, 3.75 (2H, ABq, J=17.32 Hz), 4.16 (2H, s), 5.13 (1H, d, J=5.46 Hz), 5.71 (1H, dd, J=8.18 Hz, 4.68 Hz), 6.67 (1H, s), 6.85 (1H, s), 7.11 (2H, s), 7.63 (1H, s), 9.47 (1H, d, J=8.18 Hz).

(3) 7β-[2-(2-Aminothiazol-4-yl)-2-(Z)-(hydroxyimino)acetamido]-3-[(2-methyl-1,3,4-oxadiazol-5-yl)methylthio)]-3-cephem-4-carboxylic acid IR (KBr): 3317.0, 1766.5, 1668.1, 1596.8 cm$^{-1}$; NMR (DMSO-d$_6$, δ): 2.46 (3H, s), 3.51, 3.71 (2H, ABq, J=16.98 Hz), 4.20, 4.28 (2H, ABq, J=15.02 Hz), 5.03 (1H, d, J=4.80 Hz), 5.67 (1H, dd, J=8.12 Hz, 4.74 Hz), 6.65 (1H, s), 7.13 (2H, s), 9.45 (1H, d, J=8.18 Hz), 11.44 (1H, s).

EXAMPLE 22

The following compounds were obtained according to a similar manner to that of Example 17.

(1) 7β-[2-(2-Aminothiazol-4-yl)-2-(Z)-(hydroxyimino)acetamido]-3-[(pyrazol-4-yl)methylthio)]-3-cephem-4-carboxylic acid IR (KBr): 3315.0, 1764.5, 1664.3, 1604.5 cm$^{-1}$; NMR (DMSO-d$_6$, δ): 3.80 (2H, d, J=3.9 Hz), 4.11 (2H, s), 5.12 (1H, d, J=4.6 Hz), 5.69 (1H, dd, J=8.2 Hz, 6.5 Hz), 6.19 (1H, d, J=2.2 Hz), 6.68 (1H, s), 7.12 (2H, s), 7.61 (1H, d, J=2.2 Hz), 9.44 (1H, d, J=8.2 Hz), 11.29 (1H, s), 12.99 (1H, br s).

(2) 7β-[2-(5-Amino-1,2,4-thiadiazol-3-yl)-2-(Z)-hydroxyiminoacetamido]-3-[(pyrazol-4-yl)methylthio]-3-cephem-4-carboxylic acid IR (KBr): 3307.3, 1764.5, 1670.1, 1619.9, 1525.4 cm$^{-1}$; NMR (DMSO-d$_6$, δ): 3.76 (3H, s), 4.02 (2H, s), 5.12 (1H, d, J=4.70 Hz), 5.75 (1H, dd, J=8.60 Hz, 4.86 Hz), 7.55 (2H, s), 8.06 (2H, s), 9.45 (1H, d, J=8.64 Hz).

(3) 7β-2-[2-(2-Aminothiazol-4-yl)-2-(Z)-(hydroxyimino)acetamido]-3-[2-(pyrazol-4-yl)ethylthio]-3-cephem-4-carboxylic acid IR (KBr): 3278.4, 1764.5, 1666.2, 1608.2, 1537.0 cm$^{-1}$; NMR (DMSO-d$_6$, δ): 2.65, 2.68 (ABq, 2H, J=4.84 Hz), 3.00 (2H, t, J=7.42 Hz), 3.72 (2H, s), 5.16 (1H, d, J=4.62 Hz), 5.70 (1H, dd, J=8.10 Hz, 4.60 Hz), 6.86 (1H, s), 7.12 (2H, s), 7.46 (2H, s), 9.46 (1H, d, J=8.18 Hz), 11.30 (1H, s)

(4) 7β-2-[2-(2-Aminothiazol-4-yl)-2-(Z)-(hydroxyimino)acetamido]-3-[(3-methyl-1,2,4-thiadiazol-5-yl)methylthio]-3-cephem-4-carboxylic acid IR (KBr): 3303.5, 1764.5, 1668.1, 1606.4 cm$^{-1}$; NMR (DMSO-d$_6$, δ): 2.54 (3H, s), 3.49, 3.59 (2H, ABq, J=16.94 Hz), 4.45, 4.52 (2H, ABq, J=15.74 Hz), 5.01 (1H, d, J=4.80 Hz), 5.65 (1H, dd, J=8.16 Hz, 4.74 Hz), 6.64 (1H, s), 7.15 (2H, s), 9.43 (1H, d, J=8.22 Hz), 11.50 (1H, s).

(5) 7β-[2-(2-Aminothiazol-4-yl)-2-(Z)-(hydroxyimino)acetamido]-3-[(2-methyl-1,3,4-thiadiazol-5-yl)methylthio]-3-cephem-4-carboxylic acid IR (KBr): 3193.5, 1770.3, 1668.1, 1602.6, 1527.3 cm$^{-1}$; NMR (DMSO-d$_6$, δ): 2.68 (3H, s), 3.35 (2H, s), 4.55, 4.61 (2H, ABq, J=15.22 Hz), 5.12 (1H, d, J=4.72 Hz), 5.72 (1H, dd, J=8.20 Hz, 4.66 Hz), 6.67 (1H, s), 7.13 (2H, s), 9.47 (1H, d, J=8.26 Hz), 11.30 (1H, s).

EXAMPLE 23

Under nitrogen atomosphere, a solution of aluminium chloride (2.65 g) in anisole (5.7 ml) was added dropwise to a solution of diphenylmethyl 7β-[2-(2-aminothiazol-4-yl)-2-(Z)-(trityloxyimino)acetamido]-3-[(1-tritylpyrazol-4-yl)methylthio]-3-cephem-4-carboxylate (3.32 g) in a mixture of anisole (5.7 ml) and nitromethane (22.5 ml) at −24° C. After stirring for 1 hour at the same temperature, the reaction was quenched with 1N hydrochloric acid (22.5 ml). The mixture was poured into a mixture of water and ethyl acetone. The aqueous layer was separated and the organic layer was reextracted with water. The combined aqueous layer was concentrated in vacuo, chromatographed on a HP-20 column (eluent: water-methanol). After the concentration, the resulting precipitate was collected by filtration to afford 7β-[2-(2-aminothiazol-4-yl)-2-(Z)-(hydroxyimino)acetamido]-3-[(pyrazol-4-yl)methylthio]-3-cephem-4-carboxylic acid IR (KBr): 3203, 1762, 1660, 1600 cm$^{-1}$; NMR (DMSO-d$_6$, δ): 3.76 (2H, s), 4.02 (2H, d, J=2 Hz), 5.14 (1H, d, J=4.6 Hz), 5.69 (1H, dd, J=8.2 and 4.6 Hz), 6.68 (1H, s), 7.13 (1H, s), 7.55 (1H, s), 9.46 (1H, d, J=8.3 Hz), 11.30 (1H, s).

EXAMPLE 24

Under nitrogen atmosphere, trifluoroacetic acid (2.0 ml) was added dropwise to a solution of diphenylmethyl 7β-[2-(2-aminothiazol-4-yl)-2-(Z)-(methoxyimino)acetamido]-3-[(1,2,3-thiadiazol-5-yl)methylthio]-3-cephem-4-carboxylate (1.02 g) in anisole (1.0 ml) and dichloromethane (3.0 ml) under ice cooling. The mixture was stirred for 1 hour at room temperature, and then poured into 150 ml of isopropanol. The resulting precipitate was collected by filtration and treated on HP-20 (eluent: water-methanol) to afford 7β-[2-(2-aminothiazol-4-yl)-2-(Z)-(methoxyimino)acetamido]-3-[(1,2,3-thiadiazol-5-yl)methylthio]-3-cephem-4-carboxylic acid (193.3 mg).

IR (KBr): 3315.0, 1783.8, 1760.7, 1672.0, 1633.4 cm$^{-1}$; NMR (DMSO-d$_6$, δ): 3.75 (2H, s), 3.83 (3H, s), 4.61 (2H, s), 5.17 (1H, d, J=4.74 Hz), 5.73 (1H, dd, J=8.20 Hz, 4.70 Hz).

EXAMPLE 25

The following compounds were obtained according to a similar manner to that of Example 24.

(1) 7β-[2-(2-Aminothiazol-4-yl)-2-(Z)-methoxyimino)acetamido]-3-[(2-methyl-1,3,4-thiadiazol-5-yl)methylthio]-3-cephem-4-carboxylic acid IR (KBr): 3311.2, 1772.3, 1670.1, 1621.8, 1535.1 cm$^{-1}$; NMR (DMSO-d$_6$, δ): 2.68 (3H, s), 3.79 (2H, s), 3.83 (3H, s), 4.54, 4.62 (2H, ABq, J=15.26 Hz), 5.12 (1H, d, J=4.70 Hz), 5.72 (1H, dd, J=8.26, 4.64 Hz), 6.75 (1H, s), 7.23 (2H, s), 9.62 (1H, d, J=8.26 Hz).

(2) 7β-[2-(2-Aminothiazol-4-yl)-2-(Z)-(methoxyimino)acetamido]-3-[(3-methyl-1,2,4-thiadiazol-5-yl)methylthio]-3-cephem-4-carboxylic acid IR (KBr): 3317.0, 1768.4, 1670.1, 1608.3 cm$^{-1}$; NMR (DMSO-d$_6$, δ): 2.52 (3H, s), 3.50, 3.62 (2H, ABq, J=16.90 Hz), 3.83 (3H, s), 4.46, 4.53 (2H, ABq, J=15.74 Hz), 5.01 (1H, d, J=4.76 Hz), 5.63 (1H, dd, J=8.14 Hz, 4.68 Hz), 6.73 (1H, s), 7.25 (2H, s), 9.58 (1H, d, J=8.20 Hz).

EXAMPLE 26

Diphenylmethyl 7β-[2-(2-aminothiazol-4-yl)-2-(Z)-(acetoxyimino)acetamido]-3-[(pyrazol-4-yl)methylthio]-3-cephem-4-carboxylate (41.3 g) was suspended in methanol (420 ml) at room temperature, concentrated hydrochloric acid (24.9 ml) was added below 15° C. thereto. After the reaction mixture was stirred at room temperature for 30 minutes, concentrated hydrochloric acid (6.7 ml) was added thereto at the same temperature. After stirring at room temperature for 2 hours, poured into a mixture of ethyl acetate (1.2 l) and pH 6.86 buffer (1.5 l). The pH was adjusted to pH 5.0 with 30% aqueous sodium hydroxide, and then was adjusted to pH 6.0 with 2N-potassium hydroxide. The organic layer was separated, and herein THF (0.5 l) was added thereto with brine (1.0 l). The organic layer was washed with brine (1.0 l), dried over magnesium sulfate, and evaporated until the volume amounted to 500 ml. A mixture of IPE (500 ml) and ethyl acetate (700 ml) was added thereto. Resulting precipitate was filtered, dried under reduced pressure to afford diphenylmethyl 7β-[2-(2-aminothiazol-4-yl)-2-(Z)-(hydroxyimino)acetamido]-3-[(pyrazol-4-yl)methylthio]-3-cephem-4-carboxylate (33.6 g) as powder.

IR (KBr): 1772, 1684, 1616, 1533 cm$^{-1}$; NMR (DMSO-d$_6$, δ): 3.78–4.07 (4H, m), 5.22 (1H, d, J=4.6 Hz), 5.79 (1H, dd, J=4.6 Hz, 8.4 Hz), 6.84 (1H, s), 7.14 (1H, s), 7.24–7.53 (14H, m), 9.50 (1H, d, J=8.4 Hz), 11.32 (1H, s); FAB-Mass: 648 (M$^+$+1).

EXAMPLE 27

Under nitrogen atmosphere, diphenylmethyl 7β-[2-(2-aminothiazol-4-yl)-2-(Z)-(hydroxyimino)acetamido]-3-[(pyrazol-4-yl)methylthio]-3-cephem-4-carboxylate (33.5 g) was suspended in dichloromethane (100 ml) and anisole (35 ml). Trifluoroacetic acid (80 ml) added dropwise below 5° C. for 40 minutes. After stirring below 5° C. for 25 minutes, the reaction mixture was poured into IPE (1.8 l). Resulting precipitate was collected by filtration and dried under reduced pressure. The powder was poured into pH 6.86 buffer (550 ml). The suspension was adjusted to pH 6.9 with 2N-potassium hydroxide, then was stirred at 15° C. until insoluble material disappeared. The solution was subjected to column chromatography on HP-20 (700 ml). The column was washed with water (1.4 l) and the object compound was eluted with 25% aqueous 2-propanol. The active fractions were collected, and adjusted to pH 3.5 with 3N-hydrochloric acid. After stirring at 30° C. for 2 hours, resulting precipitate was filtered and washed with water (50 ml) two times. The precipitate was suspended in water (150 ml), and adjusted to pH 2.0 with 1N-hydrochloric acid. After stirring at room temperature for one hour, the precipitate was collected and washed with water (20 ml). The precipitate was suspended in water (150 ml) again, and then adjusted to pH 2.0 with 1N hydrochloric acid. After stirring at room temperature for one hour, it was adjusted to pH 2.8 with 2N potassium hydroxide. After stirring at the same temperature for 30 minutes, the precipitate was collected, washed with water (20 ml), and dried under reduced pressure to afford 3.75 hydrates of 7β-[2-(2-aminothiazol-4-yl)-2-(Z)-(hydroxyimino)acetamido]-3-[(pyrazol-4-yl)methylthio]-3-cephem-4-carboxylic acid as crystal (9.7 g).

IR (KBr): 1763, 1647, 1603, 1541 cm−1; NMR (DMSO-$d_6$, δ): 3.69, 3.74 (2H, ABq, J=14.2 Hz), 3.99, 4.06 (2H, ABq, J=13.4 Hz), 5.15 (1H, d, J=4.6 Hz), 5.69 (1H, dd, J=4.6 Hz, 8.2 Hz), 6.71 (1H, s), 7.30 (2H, m), 7.56 (2H, s), 9.48 (1H, d, J=8.2 Hz), 11.41 (1H, s); FAB-Mass: 481 (M+); Elemental Analysis Calcd. for $C_{16}H_{22.5}N_7O_{8.75}S_3$: C, 35.00, H, 4.13, N, 17.86, S, 17.52; Found C, 34.71, H, 3.84, N, 17.79, S, 17.30.

EXAMPLE 28

To a solution of 7β-[2-(2-aminothiazol-4-yl)-2-(Z)-(hydroxyimino)acetamido]-3-[(pyrazol-4-yl)methylthio]-3-cephem-4-carboxylic acid (300 mg) in N,N-dimethylacetamide (6 ml) was added potassium carbonate (81.8 mg) under ice-cooling. After stirring at room temperature for 30 minutes, cyclohexyl 1-iodoethyl carbonate (371.47 mg) was added thereto under ice-cooling. The mixture was stirred at the same temperature for 30 minutes, poured into a mixture of water and ethyl acetate and adjusted to pH 5 with 1N hydrochloric acid. The organic layer was separated, washed with water and brine, dried over magnesium sulfate, and evaporated to give (cyclohexyloxycarbonyloxy)ethyl 7β-[2-(2-aminothiazol-4-yl)-2-(Z)-(hydroxyimino)acetamido]-3-[(pyrazol-4-yl)methylthio]-3-cephem-4-carboxylate (15.8 mg).

IR (KBr): 1772.3, 1751.0, 1670.1 cm−1; NMR (DMSO-$d_6$, δ): 1.18–1.96 (13H, m), 3.85 (2H, br s), 4.05 and 4.15 (2H, ABq, J=13.1 Hz), 4.45–4.58 (1H, m), 5.16–5.19 (1H, m), 5.67–5.76 (1H, m), 6.69 (1H, s), 6.69–6.80 (1H, m), 7.16 (2H, br s), 7.57 (2H, br s), 9.44–9.49 (1H, m), 11.33 (1H, s).

EXAMPLE 29

7β-[2-(2-Aminothiazol-4-yl)-2-(Z)-(hydroxyimino)acetamido]-3-[(pyrazol-4-yl)methylthio]-3-cephem-4-carboxylic acid (283 mg) was suspended in water (100 ml) and 1.25 ml of 1N hydrochloric acid was added thereto. The mixture was stirred at 40° C. for 10 minutes and then lyophilized to afford 7β-[2-(2-aminothiazol-4-yl)-2-(hydroxyimino)acetamido]-3-[(pyrazol-4-yl)methylthio]-3-cephem-4-carboxylic acid dihydrochloride (281.8 mg).

IR (KBr): 3124.1, 1764.5, 1668.1, 1631.5, 1540.8 cm−1; NMR (DMSO-$d_6$, δ): 3.72, 3.82 (2H, ABq, J=16.86 Hz), 4.00, 4.10 (2H, ABq, J=13.58 Hz), 5.19 (1H, d, J=4.50 Hz), 5.66 (1H, dd, J=7.76 Hz, 4.54 Hz), 6.91 (1H, s), 7.70 (2H, br s), 9.75 (1H, d, J=7.78 Hz), 12.45 (1H, s); Elemental Analysis Calcd. for $C_{16}H_{15}N_7O_5S_3 \cdot 2HCl$: 12.78%; Found: 11.27%.

EXAMPLE 30

7β-[2-(2-Aminothiazol-4-yl)-2-(Z)-(hydroxyimino)acetamido]-3-[(pyrazol-4-yl)methylthio]-3-cephem-4-carboxylic acid (4.65 g) was suspended in water (27.9 ml) at room temperature, and 1N hydrochloric acid (19.3 ml) was added thereto. After stirring at 40° C. for 5 minutes, and then 1N hydrochloric acid (1.60 ml), water (4.0 ml) and ethanol (9.0 ml) was added therein at the same temperature. After stirring at 40° C. for three minutes, the mixture was further stirred at room temperature for three hours. Resulting crystal was collected by filtration, washed with water (10 ml) two times, and dried under reduced pressure to afford 7β-[2-(2-aminothiazol-4-yl)-2-(Z)-(hydroxyimino)acetamido]-3-[(pyrazol-4-yl)methylthio]-3-cephem-4-carboxylic acid.1/2 hydrochloride.3 hydrates(2.4 g) as crystals.

IR (KBr): 1770, 1734, 1670, 1541 cm−1; NMR (DMSO-$d_6$, δ): 3.71, 3.82 (2H, ABq, J=17.0 Hz), 3.99, 4.07 (2H, ABq, J=13.4 Hz), 5.16 (1H, d, J=4.6 Hz), 5.68 (1H, dd, J=4.6 Hz, 8.0 Hz), 6.80 (1H, s), 7.56 (2H, s), 9.59 (1H, d, J=8.0 Hz), 11.82 (1H, s); Elemental Analysis Calcd. for $C_{16}H_{21.5}Cl_{0.5}N_7O_8S_3$: C, 34.70, H, 3.91, N, 17.70, Cl, 3.20, S, 17.37; Found: C, 34.85, H, 3.70, N, 17.97, Cl, 3.09, S, 17.26.

EXAMPLE 31

To a solution of 1-(cyclohexyloxycarbonyloxy)ethyl 7β-[2-(2-aminothiazol-4-yl)-2-(Z)-(hydroxyimino)acetamido]-3-[(pyrazol-4-yl)methylthio]-3-cephem-4-carboxylate (166 mg) in a mixture of ethyl acetate (5 ml) and THF (5 ml) was added 4N hydrogen chloride in ethyl acetate (0.127 ml) under ice-cooling. The mixture was stirred at the same temperature for 10 minutes, and then the resulting precipitates was collected by filtration to give 1-(cyclohexyloxycarbonyloxy)ethyl 7β-[2-(2-aminothiazol-4-yl)-2-(Z)-(hydroxyimino)acetamido]-3-[(pyrazol-4-yl)methylthio]-3-cephem-4-carboxylate dihydrochloride (164 mg).

IR (KBr): 1780.0, 1735.6, 1668.1 cm−1; NMR (DMSO-$d_6$, δ): 1.12–1.91 (13H, m), 3.73–3.96 (2H, m), 4.07 and 4.17 (2H, ABq, J=13.4 Hz), 4.55 (1H, m), 5.19–5.23 (1H, m), 5.65–5.76 (1H, m), 6.72–6.79 (1H, m), 6.91 (1H, s), 6.92 (1H, s), 7.61 (2H, s), 9.72–9.75 (1H, m), 12.37 (1H, s).

EXAMPLE 32

Under nitrogen atomosphere, 1 ml of trifluoroacetic acid was added slowly to a solution of 500 mg of diphenylmethyl 7β-[2-(2-aminothiazol-4-yl)-2-(Z)-(methoxyimino)acetamido]-3-[(1-tritylpyrazol-4-yl)methylthio]-3-cephem-4-carboxylate in anisole (0.5 ml) and dichloromethane (1.5 ml) at 0° C. The mixture was warmed to a room temperature and stirred for 2 hours. The mixture was poured into IPE and the resulting precipitate was collected by filtration. The precipitate was dissolved in pH 6.86 buffer and chromatographed on a HP-20 (eluent: water-methanol). The eluate was lyophilized to afford 171.6 mg of 7β-[2-(2-aminothiazol-4-yl)-2-(Z)-(methoxyimino)acetamido]-3-[(pyrazol-4-yl)methylthio]-3-cephem-4-carboxylic acid.

IR (KBr): 1780, 1745, 1673, 1635 cm−1; NMR (D$_2$O, δ): 3.21, 3.43 (2H, ABq, J=17.4 Hz), 3.70, 3.78 (2H, ABq, J=13.9 Hz), 3.79 (3H, s), 4.95 (1H, d, J=4.68 Hz), 5.56 (1H, d, J=4.66 Hz), 6.81 (1H, s), 7.47 (2H, s).

EXAMPLE 33

The following compounds were obtained according to a similar manner to that of Example 12.

(1) Diphenylmethyl 7β-[2-(2-aminothiazol-4-yl)-2-(Z)-(trityloxyimino)acetamido]-3-[(1-trityl-1,2,4-triazol-3-yl)methylthio]-3-cephem-4-carboxylate IR (KBr): 1786, 1689, 1616 cm$^{-1}$; NMR (DMSO-d$_6$, δ): 3.9–4.0 (2H, m), 4.26 (2H, ABq, J=15 Hz), 5.05 (1H, d, J=5 Hz), 5.94 (1H, dd, J=5 Hz, 8 Hz), 6.68 (1H, s), 6.88 (1H, s), 7.0–7.7 (42H, m), 8.09 (1H, s), 9.91 (1H, d, J=8 Hz).

EXAMPLE 34

To a solution of 2-(2-aminothiazol-4-yl)-2-(Z)-trityloxyiminoacetic acid (2.87 g) in N,N-dimethylacetamide (28.7 ml) was added potassium carbonate (0.925 g) and methanesulfonyl chloride (1.04 ml) under ice-cooling. After stirring at the same temperature for 30 minutes, the mixture was added dropwise to a solution of diphenylmethyl 7β-amino-3-[(1,2,3-thiadiazol-5-yl)thio]-3-cephem-4-carboxylate (3.23 g) and bis-trimethylsilylacetamide (9.93 ml) in N,N-dimethylacetamide (32.3 ml) under ice-cooling. After being stirred at the same temperature for 45 minutes, the mixture was poured into a mixture of ice-water and ethyl acetate. The organic layer was separated, washed with water and brine, dried over magnesium sulfate, and evaporated to give diphenylmethyl 7β-[2-(2-aminothiazol-4-yl)-2-(Z)-(trityloxyimino)acetamido]-3-[(1,2,3-thiadiazol-5-yl)thio]-3-cephem-4-carboxylate (4.87 g).

IR (KBr): 1793.5, 1733.7, 1683.6 cm$^{-1}$; NMR (DMSO-d$_6$, δ): 3.60 and 3.85 (2H, ABq, J=17.6 Hz), 5.28 (1H, d, J=5.1 Hz), 6.15 (1H, dd, J=5.1 Hz, 8.5 Hz), 6.61 (1H, s), 7.00 (1H, s), 7.24–7.47 (25H, m), 8.87 (1H, s), 10.02 (1H, d, J=8.5 Hz).

EXAMPLE 35

The following compounds were obtained according to a similar manner to that of Example 15.

(1) 7β-[2-(2-Aminothiazol-4-yl)-2-(Z)-(hydroxyimino)acetamido]-3-[(1,2,4-triazol-3-yl)methylthio]-3-cephem-4-carboxylic acid IR (KBr): 3317, 1743, 1662, 1616 cm$^{-1}$; NMR (DMSO-d$_6$, δ): 3.88 (2H, m), 4.19 (2H, s), 5.12 (1H, d, J=5 Hz), 5.71 (1H, dd, J=5 Hz, 8 Hz), 6.68 (1H, s), 7.14 (2H, s), 8.37 (1H, br s), 9.48 (1H, d, J=8 Hz), 11.3 (1H, s), 13.8 (1H, br s).

EXAMPLE 36

The following compounds were obtained according to a similar manner to that of Example 17.

(1) 7β-[2-(2-Aminothiazol-4-yl)-2-(Z)-(hydroxyimino)acetamido]-3-[(1,2,3-thiadiazol-5-yl)thio]-3-cephem-4-carboxylic acid IR (KBr): 1772.3, 1652.7 cm$^{-1}$; NMR (DMSO-d$_6$, δ): 3.49 and 3.82 (2H, ABq, J=17.6 Hz), 5.26 (1H, d, J=5.0 Hz), 5.89 (1H, dd, J=8.2 Hz, 5.0 Hz), 6.65 (1H, s), 7.14 (2H, br s), 8.90 (1H, s), 9.56 (1H, d, J=8.2 Hz), 11.33 (1H, s).

EXAMPLE 37

To a suspension of 7β-[2-(2-aminothiazol-4-yl)-2-(Z)-(hydroxyimino)acetamido]-3-[(pyrazol-4-yl)methylthio]-3-cephem-4-carboxylic acid (337 g) in water (6.7 l) was added sodium hydrogen carbonate (69.7 g) at room temperature. After stirring at 30° C. till the mixture turned clear solution, a mixture of 1N-hydrochloric acid (100 ml) and 2-propanol (3.0 l) was added to thereto at room temperature. The PH of the solution was adjusted to pH 4.0 with 1N-hydrochloric acid (350 ml), the suspension was stirred for one hour at 30° C. The pH of the solution was adjusted to pH 3.3 with 1N-hydrochloric acid (185 ml), and then cooled with ice-bath. After stirring for 2 hours below 10° C., the resulting precipitate was filtered, washed with water (3 l) and 2-propanol (2 l) successively. The precipitate was dried with vacua at 40° C. for 5 hours and then at room temperature for 14 hours to afford 329 g of 7β-[2-(2-aminothiazol-4-yl)-2-(Z)-(hydroxyimino)acetamido]-3-[(pyrazol-4-yl)methylthio]-3-cephem-4-carboxylic acid containing 1/3 isopropanol as crystal.

IR (KBr): 3263, 3111, 2925, 2854, 1774, 1645, 1601, 1551, 1508, 1346 cm–1; NMR (DMSO-d$_6$, δ): 1.02 (1H, s), 1.05 (1H, s), 3.70, 3.76 (2H, ABq, J=14.2 Hz), 3.98, 4.06 (2H, ABq, J=13.4 Hz), 4.30–4.40 (0.33H, m), 5.14 (1H, d, J=4.6 Hz), 5.69 (1H, dd, J=4.6 Hz, J=8.2 Hz), 6.69 (1H, s), 7.13 (2H, s), 7.55 (2H, s), 9.45 (1H, d, J=8.2 Hz), 11.30 (1H, s).

Philips MPD 1880 X-Ray Powder Diffraction System

| 2θ | intensity |
| --- | --- |
| 7.5 | 570 |
| 8.5 | 150 |
| 11.2 | 270 |
| 17.1 | 200 |
| 18.6 | 160 |
| 19.4 | 390 |
| 19.6 | 250 |
| 20.6 | 190 |
| 21.2 | 380 |
| 22.9 | 250 |
| 24.4 | 400 |
| 25.5 | 300 |
| 25.9 | 220 |
| 28.9 | 230 |

X-ray: Monochlomated CnKα radiation

Voltage: 40 KV/Current: 30 mA

This crystal was stable in the stability test.

EXAMPLE 38

Gelatin Capsules

The capsule composition is compounded from the following ingredients.

| | |
| --- | --- |
| The compound of Example 23 | 100 parts |
| Carboxymethyl cellulose calcium | 12 parts |
| Magnesium stearate | 4 parts |
| Total | 116 parts |

The ingredients are admixed, filled into hard gelatin capsules in conventional manner. Each capsule is an oral dosage unit composition containing 100 mg of active ingredient.

What we claim is:
1. A compound of the formula:

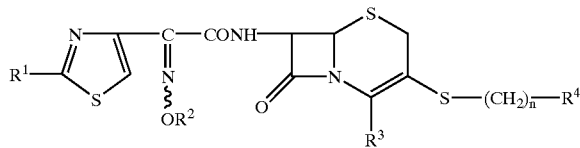

wherein $R^1$ is amino or protected amino;
$R^2$ is hydrogen, lower alkyl or hydroxy protective group;
$R^3$ is carboxy or protected carboxy;
$R^4$ is an unsubstituted 5, 6 or 7-membered heteromonocyclic group containing two nitrogen atoms as heteroatoms, and which optionally further contains one oxygen or sulfur atom; or $R^4$ is said 5, 6 or 7-membered heteromonocyclic group substituted by 1 to 4 groups selected from the group consisting of lower alkyl, lower alkoxy, lower alkylthio, lower alkylamino, cyclo(lower)alkyl, cyclo(lower)alkenyl, halogen, amino, protected amino, protected hydroxy, cyano, nitro, carboxy, hydroxy(lower)alkyl, amino(lower)alkyl, and carbamoyloxy; and
n is 1 or 2;
or a pharmaceutically acceptable salt thereof, including all geometrical isomers, stereoisomers, solvates or hydrates thereof.
2. The compound of claim 1, wherein
$R^4$ is said unsubstituted or substituted 5, 6 or 7-membered heteromonocyclic group containing two nitrogen atoms as heteroatoms, which contains one oxygen or sulfur atom, and which is bonded to the adjacent —$(CH_2)_n$ group by a carbon atom in the ring.
3. The compound of claim 1, wherein $R^4$ is said unsubstituted or substituted 5, 6 or 7-membered unsaturated heteromonocyclic ring containing two nitrogen atoms as heteroatoms, which ring is selected from the group consisting of pyrazole, pyrazoline, imidazole, imidazoline, pyrimidine, and a partially hydrogenated compound thereof, pyridazine, and a partially hydrogenated compound thereof, and pyrazine, and a partially hydrogenated compound thereof.
4. The compound of claim 1, wherein $R^4$ is selected from the group consisting of 1,2,5-thiadiazole, 1,2,4-thiadiazole, 1,2,3-thiadiazole, 6H-1,2,5-thiadiazine and hydrogenated compounds thereof.
5. The compound of claim 1, wherein $R^4$ is selected from the group consisting of 1,2,3-oxadiazole, 1,2,5-oxadiazole, 1,2,4-oxadiazole, 6H-1,2,5-oxadiazine and hydrogenated compounds thereof.
6. The compound of claim 1, wherein $R^4$ is selected from the group consisting of pyrazolidine, imidazolidine, piperazine, 1,3-diazacyclohexane and 1,2-diazacyclohexane.
7. The compound of claim 1, wherein $R^4$ is selected from the group consisting of 4-methyl-1,2,3-thiadiazol-5-yl, pyrazol-4-yl, 1-methylpyrazol-4-yl, 1,2,5-thiadiazol-3-yl, 2-methyl-1,3,4-thiadiazol-5-yl, 3-methyl-1,2,4-thiadiazol-5-yl-imidazol-2-yl, 2-methyl-1,3,4-oxadiazol-5-yl, pyradin-2-yl, pyrimidin-4-yl, pyridazin-3-yl, 1,2,3-thiadiazol-4-yl and 1,2,3-thiadiazol-5-yl.
8. The compound of claim 1, wherein in $R^4$, said 5,6 or 7-membered heteromonocyclic group is substituted by one to four groups selected from the group consisting of methyl, ethyl, propyl, methoxy, ethoxy, propoxy, methylthio, ethylthio, methylamino, ethylamino, cyclopentyl, cyclohexyl, cyclohexenyl, cyclohexadienyl, halogen, amino, protected amino, protected hydroxy, cyano, nitro, carboxy, hydroxymethyl, hydroxyethyl, aminomethyl, aminoethyl, and carbamoyloxy.
9. The compound of claim 1, which is
7β-[2-(2-aminothiazol-4-yl)-2-(Z)-(hydroxyimino)acetamido]-3-[(pyrazol-4-yl)methylthio]-3-cephem-4-carboxylic acid or a pharmaceutically acceptable salt thereof.
10. A process for preparing a compound of the formula:

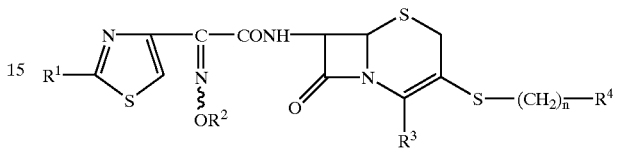

wherein $R^1$ is amino or protected amino;
$R^2$ is hydrogen, lower alkyl or hydroxy protective group;
$R^3$ is carboxy or protected carboxy;
$R^4$ is optionally substituted 5, 6 or 7-membered heteromonocyclic group containing two nitrogen atoms as heteroatoms, and which optionally further contains one oxygen or sulfur atom; and
n is 1 or 2,
or pharmaceutically acceptable salt thereof, which comprises
(1) reacting a compound of the formula (II):

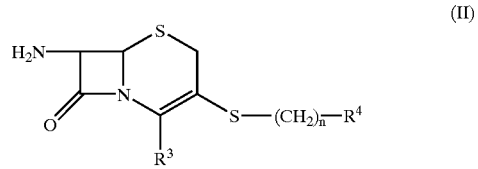

wherein $R^3$, $R^4$ and n are each defined above, or a reactive compound thereof at the amino group, or a salt thereof with a compound of the formula (III):

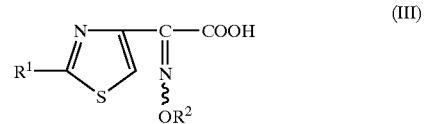

wherein $R^1$ and $R^2$ are each as defined above, or a reactive compound thereof at the carboxy group, or a salt thereof to give a compound of the formula (I):

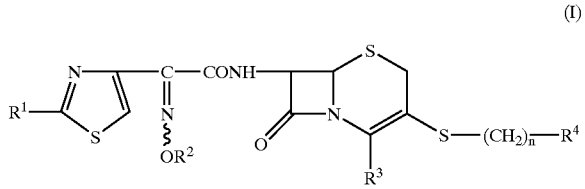

wherein $R^1$, $R^2$, $R^3$, $R^4$ and n are each as defined above, or a salt thereof.
11. The process of claim 10, wherein said reaction of said compound (II) with said compound (III) is conducted in the presence of a solvent.

12. The process of claim 10, wherein said reactive compound at the amino group of the compound (II) comprises a Schiff's base imino or enamine thereof, a silyl compound thereof or a compound formed by reaction of the compound (II) with phosgene or phosphorus trichloride.

13. The process of claim 10, wherein said reactive compound at the carboxy group of the compound (III) comprises an acid halide, acid anhydride, ester, amide or azide thereof.

14. The process of claim 1, wherein said solvent comprises water, methanol, ethanol, acetone, dioxane, acetonitrile, chloroform, methylene chloride, ethylene chloride, tetrahydrofuran, ethyl acetate, pyridine or N,N-dimethylformamide.

15. The process of claim 11, wherein the compound (III) is in free acid form or the salt form thereof, and said reaction is effected in the presence of a condensing agent.

16. A pharmaceutical composition which comprises, as an active ingredient, a compound of claim 1, or a pharmaceutically acceptable salt thereof in admixture with a pharmaceutically-acceptable carrier.

17. A method for treating a disease caused by a pathogenic microorganism, which comprises administering an effective amount of one or more compounds of claim 1, or a pharmaceutically acceptable salt thereof to a mammal in need thereof.

18. The method of claim 17, wherein said mammal is human.

19. The method of claim 17, wherein said disease is caused by Gram-negative or Gram-positive bacteria.

20. The method of claim 17, wherein said disease is caused by *S. aureus, E. coli* or *H. influenzae.*

* * * * *